United States Patent
Abraham

(10) Patent No.: US 8,403,858 B2
(45) Date of Patent: *Mar. 26, 2013

(54) IMAGE GUIDED CATHETERS AND METHODS OF USE

(75) Inventor: Theodore P. Abraham, Baltimore, MD (US)

(73) Assignee: Perceptive Navigation LLC, Baltimore, MD (US)

( * ) Notice: Subject to any disclaimer, the term of this patent is extended or adjusted under 35 U.S.C. 154(b) by 31 days.

This patent is subject to a terminal disclaimer.

(21) Appl. No.: 11/782,991

(22) Filed: Jul. 25, 2007

(65) Prior Publication Data

US 2008/0091109 A1   Apr. 17, 2008

Related U.S. Application Data

(60) Provisional application No. 60/851,451, filed on Oct. 12, 2006.

(51) Int. Cl.
*A61B 8/14* (2006.01)

(52) U.S. Cl. ........ 600/466; 600/464; 600/462; 600/467; 600/407; 600/437

(58) Field of Classification Search .............. 600/461, 600/462, 463, 464, 466, 467, 470
See application file for complete search history.

(56) References Cited

U.S. PATENT DOCUMENTS

| | | | |
|---|---|---|---|
| 3,556,079 A | | 1/1971 | Omizo |
| 3,612,050 A | * | 10/1971 | Sheridan ............... 604/166.01 |
| 4,092,867 A | * | 6/1978 | Matzuk ..................... 73/609 |
| 4,327,709 A | * | 5/1982 | Hanson et al. ............. 600/18 |
| 4,869,258 A | | 9/1989 | Hetz |
| 5,011,469 A | * | 4/1991 | Buckberg et al. ......... 604/6.11 |
| 5,106,368 A | * | 4/1992 | Uldall et al. ................ 604/43 |
| 5,159,931 A | | 11/1992 | Pini |
| 5,181,514 A | | 1/1993 | Solomon et al. |
| 5,454,373 A | | 10/1995 | Koger et al. |
| 5,505,088 A | * | 4/1996 | Chandraratna et al. ...... 73/623 |
| 5,509,909 A | * | 4/1996 | Moy ........................ 604/540 |
| 5,701,901 A | | 12/1997 | Lum et al. |
| 5,704,361 A | | 1/1998 | Seward |
| 5,967,984 A | | 10/1999 | Chu et al. |
| 5,997,497 A | | 12/1999 | Nita et al. |

(Continued)

FOREIGN PATENT DOCUMENTS

CA   2 376 103   3/2001

OTHER PUBLICATIONS

International Search Report corresponding to International Application No. PCT/US2007/081185 dated Jul. 10, 2008.

(Continued)

*Primary Examiner* — Jacqueline Cheng
*Assistant Examiner* — Joel F Brutus
(74) *Attorney, Agent, or Firm* — Cameron LLP

(57) ABSTRACT

An interventional medical device that incorporates an imaging system may be minimally invasive and equipped with an anchoring portion at a proximal end for securing the device to a human body. A luer lock may be utilized at the proximal end, for example, for introducing a syringe. The medical device can be in the form of sheaths, catheters, and interventional devices, particularly those suitable for minimally invasive procedures in the pericardium. The imaging system comprises one or more ultrasound transducers and can be used to guide the device to a target area and to perform a procedure and/or provide access to a target area for performing a procedure via a plurality of lumen. In one embodiment, a micro-electro-mechanical system may be utilized to monitor pressure within a human body.

28 Claims, 15 Drawing Sheets

U.S. PATENT DOCUMENTS

| | | | |
|---|---|---|---|
| 6,068,638 | A | 5/2000 | Makower |
| 6,149,598 | A | 11/2000 | Tanaka |
| 6,162,179 | A | 12/2000 | Moore |
| 6,254,573 | B1 * | 7/2001 | Haim et al. ............... 604/157 |
| 6,306,097 | B1 | 10/2001 | Park et al. |
| 6,572,551 | B1 | 6/2003 | Smith et al. |
| 6,592,559 | B1 | 7/2003 | Pakter et al. |
| 6,685,648 | B2 | 2/2004 | Flaherty |
| 6,689,062 | B1 | 2/2004 | Mesallum |
| 6,726,677 | B1 * | 4/2004 | Flaherty et al. ............ 604/528 |
| 7,100,614 | B2 | 9/2006 | Stevens et al. |
| 7,270,634 | B2 | 9/2007 | Scampini et al. |
| 7,488,289 | B2 | 2/2009 | Suorsa et al. |
| 7,713,190 | B2 | 5/2010 | Brock et al. |
| 7,860,555 | B2 | 12/2010 | Saadat |
| 2001/0023323 | A1 * | 9/2001 | Nishtala et al. ............ 600/567 |
| 2002/0123698 | A1 * | 9/2002 | Garibotto et al. ........... 600/585 |
| 2003/0139677 | A1 * | 7/2003 | Fonseca et al. ............. 600/508 |
| 2003/0229286 | A1 * | 12/2003 | Lenker ........................ 600/462 |
| 2004/0015193 | A1 * | 1/2004 | Lamson et al. ................ 607/9 |
| 2005/0090709 | A1 | 4/2005 | Okada et al. |
| 2006/0106315 | A1 | 5/2006 | Edens |
| 2007/0293724 | A1 * | 12/2007 | Saadat et al. ................ 600/156 |

OTHER PUBLICATIONS

Non-final Office Action issued Oct. 13, 2011 in U.S. Appl. No. 12/285,779 related as continuation-in-part to the present application.
European Examination Report issued Apr. 26, 2012 citing D1 (US 3,556,079), D2 (US 2006/106315), D7 (US 6,149,598) and D9 (US 5,704,361).

* cited by examiner

IMAGE GUIDED CATHETERS AND METHODS OF USE

CROSS-REFERENCE

This application claims priority to provisional U.S. Application Ser. No. 60/851,451, filed Oct. 12, 2006.

TECHNICAL FIELD

Illustrated and disclosed aspects relate to medical devices having incorporated imaging systems, more particularly to minimally invasive interventional medical devices having incorporated ultrasound imaging systems.

BACKGROUND

Ultrasound operates by creating an image from sound in three steps—producing a sound wave, receiving echoes, and interpreting those echoes to create an image. Invasive ultrasonic apparatus is known for imaging areas of the human body and has found many diagnostic and therapeutic uses such as guiding therapeutic instruments through a catheter to a field of view within a human body. For example, U.S. Pat. No. 5,704,361 to Seward et al. discloses a volumetric image ultrasound transducer underfluid catheter system. FIGS. 2-9 and 11-12 and their attendant description, for example, suggest specific methods of intervention for imaging purposes in the vicinity of a human heart. To reach such an area of interest within a human body, an ultrasound imaging and hemodynamic catheter may be advanced via the superior vena cava of the heart to a tricuspid valve annulus. A distal end of a cylindrical body includes a guide wire access port and a guide wire provides a means of assuring that the catheter reaches a target for imaging. A surgical tool may be fed through the catheter to the area imaged.

U.S. Pat. No. 6,572,551 to Smith et al. provides another example of an imaging catheter. Tools may be incorporated in an exemplary catheter, including suction, guide wire, or an ablation electrode.

U.S. Pat. No. 5,967,984 to Chu et al. describes an ultrasound imaging catheter with a cutting element which may be an electrode wire or a laser fiber. FIGS. 1 and 2 also describe a balloon 14 and a means to inflate the balloon. The balloon, for example, may be utilized to dilate a vessel having strictures imaged via the imaging catheter.

Other imaging catheters are known. For example, U.S. Pat. No. 6,162,179 to Moore teaches bending (using a pull wire) an acoustic window into a known and repeatable arc for improved three dimensional imaging. U.S. Pat. No. 6,306,097 to Park et al. discloses an ultrasound imaging catheter whereby a first lumen provides access for an ultrasound imaging catheter and a second lumen provides a working port for a tool.

In view of these references, it is suggested that ultrasound is a common imaging technique that can be used to visualize internal organs. All the above-cited references are incorporated by reference in their entirety as to any teachings which may be deemed essential to an understanding of illustrated and discussed aspects and embodiments of devices and methods herein.

Ultrasound has many uses in medical applications. For example, ultrasound is routinely used during pregnancy to provide images of the fetus in the womb. Generally, a water-based gel is applied to the patient's skin, and a hand-held probe, called a transducer, is placed directly on and moved over the patient. The probe typically contains a piezoelectric element that vibrates when a current is applied. In ultrasound devices, a sound wave is typically produced by creating short, strong vibrational pulses using a piezoelectric transducer. The sound wave is reflected from tissues and structures and returns an echo, which vibrates the transducer elements and turns the vibration into electrical pulses. The electrical pulses are then sent to an ultrasound scanner where they are transformed into a digital image.

While general-purpose ultrasound machines may be used for most imaging purposes, certain procedures require specialized apparatus. For example, in a pelvic ultrasound, organs of the pelvic region can be imaged using either external or internal ultrasound. In contrast, echocardiography, which is used in cardiac procedures, can require specialized machines to take into account the dynamic nature of the heart.

Ultrasound has advantages over other imaging methods such as magnetic resonance imaging (MRI) and computed tomography (CT). For example, ulatrasound is a relatively inexpensive compared to those techniques. Ultrasound also is capable of imaging muscle and soft tissue very well, can delineate interfaces between solid and fluid filled spaces, and shows the structure of organs. Ultrasound renders live images and can be used to view the operation of organs in real time. Ultrasound has no known long-term side effects and generally causes little to no discomfort to a patient. Further, ultrasound equipment is widely available, flexible, and portable. However, ultrasound does have some drawbacks. When used on obese patients, image quality is compromised as the overlying adipose tissue scatters the sound and the sound waves are required to travel greater depths, resulting in signal weakening on transmission and reflection back to the transducer. Even in non-obese patients, depth penetration is limited, thereby making it difficult to image structures located deep within the body. Further, ultrasound has trouble penetrating bone and, thus, for example, ultrasound imaging of the brain is limited. Ultrasound also does not perform well when there is gas present (as in the gastrointestinal tract and lungs). Still further, a highly skilled and experienced ultrasound operator is necessary to obtain quality images. These drawbacks do not, however, limit the usefulness of ultrasound as a medical diagnostic and treatment tool.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter.

Illustrative aspects described herein include a minimally invasive, interventional medical device that can provide ultrasound imaging coupled together with one or more interventional capabilities. The frequencies present in a sound wave output by such a device can range between 1 and 13 MHz.

The ultrasound features of the device can serve to guide and facilitate surgical procedures performed with the device. For example, a medical professional such as a surgeon can receive direct vision of a targeted area in real time. Moreover, use of a device according to one or more aspects herein can significantly reduce the extent of surgical intervention required for a particular procedure. Thus, for example, many procedures can be performed through minimally invasive surgical techniques where more invasive surgical procedures have been previously required, for example, entry through a blood vessel in a human leg to reach a human heart using a guide wire and catheter.

In accordance with one or more aspects, a medical device is provided that comprises one or more ultrasound transducers coupled or associated with a syringe element for fluid withdrawal or delivery. A wide variety of other interventional elements can be incorporated into such a device via a plurality of lumen.

According to other aspects, such a device can be utilized in a variety of biopsy procedures and provide accurate guidance and imaging of a targeted area. For example, biopsies of various organs and tissue such as myocardial, brain, muscle, lung, liver, kidney uterine, ovarian, esophageal, stomach, intestinal, tumors, or other patient organs or tissue may be accurately performed with such a device.

Other vascular structures also can be effectively accessed and treated as desired with such a device including e.g. arteries, veins, and lymphatics. Other hollow structures such as the gastrointestinal tract, genitourinary tract, and respiratory system also can be accessed and treated using a device according to aspects described herein.

Devices as discussed herein can be effectively utilized for intracardiac treatments via pericardial access, without entry through blood vessels. Such devices can also be especially useful in diagnosing and treating loculated or compartmentalized effusions in the heart (pericardial), abdomen (ascites), chest, or abcesses in any organ or body cavity. The real-time imaging that can be provided by devices of the invention can allow safe and accurate access to multiple compartments and ensure safe and complete drainage.

In some embodiments according to aspects herein, an interventional ultrasound device may include an elongate body having a proximal end and a distal end. In accordance with conventional nomenclature, a "proximal" end as used herein designates the end of a device closest to the personnel operating the device, and a "distal" end designates the opposite end, for example, the end placed within the patient. In accordance with one or more aspects described herein, an interventional ultrasound device can have one or more lumen extending through the elongate body and one or more ultrasound transducers embedded in the elongate body near the distal end to provide imaging of an area within a patient as the elongate body is passed therethrough.

According to other aspects, at the proximal end of such a device, an anchoring portion is provided for anchoring the device to a human body once the device is image-guided and thus inserted therein so that the distal end reaches a region of interest within the human body in as minimally invasive a procedure as possible. According to aspects herein, the elongate body of such a device may be formed from one or more of a variety of materials such as silicone, Teflon, polyurethane, PVC, and/or elastomeric hydrogel. According to some aspects, the elongate body may be cylindrical in shape and may include, for example, a catheter or vascular sheath.

In use, such as in a minimally invasive surgical procedure, an elongate body member of such a device may be advanced to a target site of a patient while using the one or more ultrasound transducers to guide insertion of the device; and the one or more ultrasound transducers can image the target site while the minimally invasive surgical procedure is performed with the device anchored at the device by the anchoring portion.

In an exemplary procedure of accessing the pericardium and performing effusion, such a device can be advanced to a patient's pericardium while using the one or more ultrasound transducers to guide insertion and advancement of the elongate body of the device. Such an exemplary procedure can include puncturing the pericardial lining as the device is advanced while imaging the pericardial lining using the one or more ultrasound transducers; further advancing the elongate body into the pericardium; inserting a guide wire through the lumen of the elongate body; advancing a sheath over the guide wire; and draining pericardial fluid or applying other therapeutic measures.

A further exemplary procedure for accessing the pericardium and performing a procedure on a target site of the pericardium can include advancing a device to a patient's pericardium while using the one or more ultrasound transducers to guide insertion and advancement of the device's elongate body; puncturing the pericardial lining while imaging the pericardial lining using the one or more ultrasound transducers; advancing the elongate body into the pericardium; optionally injecting material into the pericardium through the elongate body to create a pericardial pocket; inserting a guide wire through the lumen; advancing a sheath over the guide wire; inserting interventional and/or diagnostic devices through the sheath; and performing a pericardial procedure using the interventional and/or diagnostic devices.

These and other aspects will be discussed with reference to the drawings, a brief description of which follows.

BRIEF DESCRIPTION OF THE DRAWINGS

The above-described aspects and embodiments of devices and procedures and other features and advantages can be appreciated and understood by reference to the following detailed description when considered in connection with the accompanying drawings wherein.

DETAILED DESCRIPTION

Figure 1A:
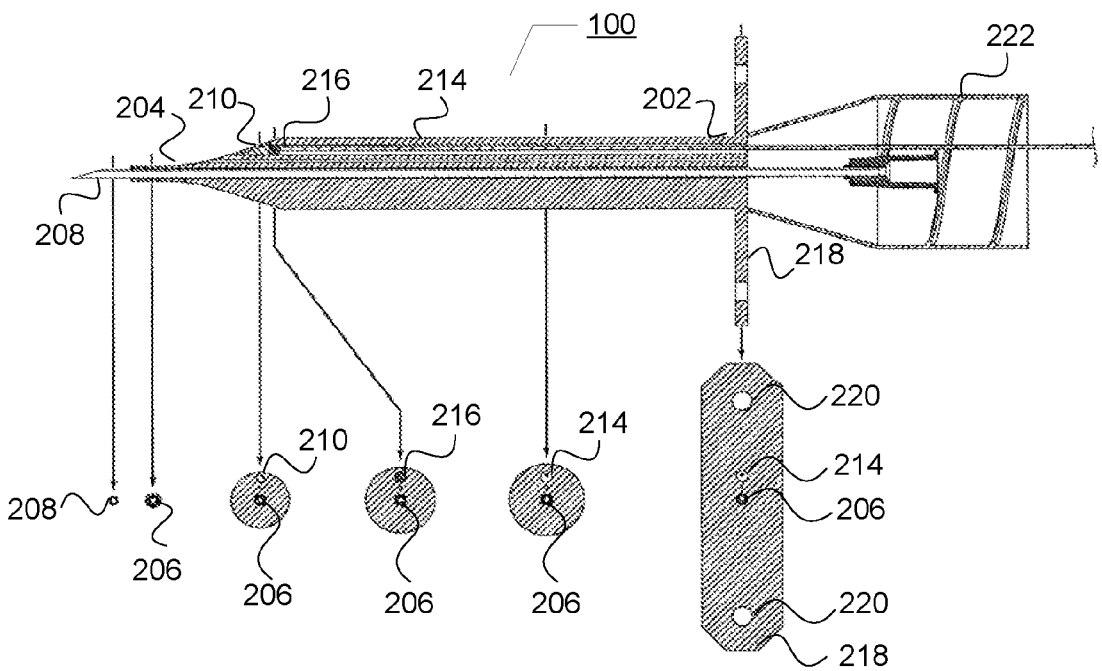
FIG. 1 shows a side cross-sectional view of one embodiment of a minimally invasive device in accordance with aspects described herein wherein FIG. 1A includes six cross-sectional views along the length of the depicted embodiment.
FIG. 1B provides a cross-sectional view of the embodiment of FIG. 1A and FIG. 1C provides further detail of the distal end of the device of FIG. 1A.

The aspects summarized above can be embodied in various forms. The following description shows, by way of illustration, combinations and configurations in which the aspects can be practiced. It is understood that the described aspects and/or embodiments are merely examples. It is also understood that other aspects and/or embodiments can be utilized, and that structural and functional modifications can be made, without departing from the scope of the present disclosure.

Minimally invasive procedures can provide physicians with access to internal organs and structures via a small number of incisions in the patients' body. Using this approach, the treatment area can be accessed by creating a small number of incisions and inserting cannulas or sleeves through the incisions to provide entry ports through which instruments are passed. Alternatively, access to the treatment area can sometimes be obtained using a natural bodily opening such as the throat or rectum. In such procedures, a cannula or sleeve can be inserted into the bodily opening and surgical instruments are passed, either through the cannula/sleeve or directly through the bodily opening, to the treatment site.

Minimally invasive procedures can generally be preferable over open procedures because they can require only small incisions, can reduce trauma to the body, can lessen recovery time, and can reduce costs. The medical instruments used in performing such procedures can generally be similar to those used in open surgical procedures except they can include an extension such as a tubular extension between the end of the instrument entering the surgical field (i.e., the operable end of the tool, instrument or device) and the portion gripped by the surgeon.

While minimally invasive procedures can provide numerous advantages over open procedures, they generally do not provide a physician with a direct view of the targeted sites. Further, many parts of the anatomy are rather complex and/or small and, thus, require particular precision and delicate handling. Therefore, it can be necessary to provide precise imaging techniques for use during minimally invasive procedures.

In certain minimally invasive procedures, a visualization tool or guide, such as an endoscope, laparoscope, laryngoscope, etc., also can be inserted to the treatment site along with the medical instruments so that, as the surgeon manipulates the surgical instruments outside of the surgical site, he or she is able to view the procedure on a monitor.

For example, endoscopes are used during an endoscopic procedure, which is a procedure performed on the digestive system. The endoscope is a flexible tube that incorporates a camera and light and allows visualization inside the body. The endoscope can be inserted through the mouth or anus to access any portion of the digestive system. While endoscopy does not require the creation of incisions and allows for visualization of a site prior to and during surgery, endoscopes are relatively expensive and are obscured by blood and other biological materials. Further, endoscopes are capable only of viewing the surfaces of structures such as nasal passages or the lining of the colon, and cannot provide visualization of what is inside of or beyond structures.

Laparoscopes are used during laparoscopic procedures, which are performed on a patient's abdomen or pelvis, including the fallopian tubes, ovaries, uterus, small bowel, large bowel, appendix, liver, and gallbladder. During a laparoscopic procedure, a telescopic instrument called a laparoscope is inserted into the abdomen through a small incision at the belly button. A camera attached to the laparoscope allows surgeons to view inside the abdomen and perform the procedures without having to make a large incision. Usually, four more small incisions are made in the abdomen to accommodate surgical instruments, typically through cannulas or sleeves, during the procedure. As with endoscopes, laparoscopes are capable only of viewing structures and cannot provide visualization of what is inside of or beyond structures.

Another common imaging technique that can be used to visualize a patient's internal structures is tomography. Tomography provides imaging by sections or sectioning. Computed tomography (CT) can use digital geometry processing to generate a three-dimensional image of the internals of an object from a large series of two dimensional X-ray images taken around a single axis of rotation. However, CT is regarded as a moderate to high radiation diagnostic technique. Further, because CT scans rely on intravenously administered contrast agents in order to provide high image quality, there is a risk associated with the contrast agents. Certain patients may experience severe and even life-threatening allergic reactions to the contrast agents. Further, the contrast agents can induce kidney damage. With patients who have preexisting renal insufficiency, preexisting diabetes, or reduced intravascular volume, this risk is increased. Further, CT cannot be used during a procedure and, thus, is not sufficient for use in procedures on anatomical structures that are subject to motion such as, for example, the heart.

Magnetic resonance imaging (MRI), formerly referred to as magnetic resonance tomography (MRT) or nuclear magnetic resonance (NMR), is a method used to visualize the inside of living organisms as well as to detect the composition of geological structures. Like CT, MRI is not performed during a procedure and is insufficient for use in procedures on anatomical structures that are subject to motion. Further, MRI devices are very expensive and require significant upkeep costs. While CT scanner uses ionizing radiation, X-rays, to provide images, MRI uses radio frequency signals. Thus, CT is good for dense tissue (e.g. bone), while MRI is best suited for soft (non-calcified) tissue. MRI also cannot be performed on patients with pacemakers because arrhythmias or even death can result. Ferromagnetic foreign bodies or metallic implants (e.g. surgical prosthesis) also present potential risks for MRI. Interaction between the magnetic and radiofrequency fields with these bodies can cause the bodies to move and result in trauma, and radiofrequency induction heating of the bodies can also cause thermal injury. Further, some individuals with even mild claustrophobia may be unable to tolerate an MRI scan.

The devices and methods relating to an embodiment of an ultrasound imaging catheter primarily illustrated in FIGS. 1-8 and described herein can be used in a wide variety of minimally invasive surgical procedures. In addition, one skilled in the art will appreciate that the aspects and embodiments of FIGS. 1-8, although advantageously suited for such procedures on humans, can be used in veterinary procedures and in open medical techniques as well. Further, while the devices of the present invention are described with particular reference to catheters, this shall not be construed as limiting the devices to the these embodiments, however, as it is contemplated and thus within the scope of the illustrated devices to adapt the devices described herein so as to be in the form of any type of minimally invasive device (e.g. syringes, sheaths, wires, forceps, biopsy instruments, clamps, retractors, etc.).

Further, while certain devices, systems and methods are described herein with particular reference to pericardial access devices, systems, and methods, this shall not be construed as limiting, as it is contemplated to adapt the devices, systems and methods described herein so as to be used in any of a number of procedures, including, but not limited to, various cardiovascular procedures, general micro-surgery, biopsy, drug and device delivery, vascular procedures, urology, thoracic procedures, otorhinolaryngology (ear, nose and throat), orthopedic procedures, neurosurgery, gynecologic procedures, gastroenterologic and general procedures, colon and rectal procedures, pericardiocentesis, thoracentesis, ascites tap, ventricular lead placements, and electrical and electromechanical mapping of the heart. As such, it is contemplated that the specific design parameters, other characteristics set forth hereinafter, and methods in relation thereto can be modified as required so as to provide the appropriate dimensions and geometries as required to perform such other techniques. For example, the length and diameter of the device as herein described, is adapted to suit the particular conditions for a given procedure but can be modified to suit conditions for a different procedure. Thus, the disclosure to follow should be construed as illustrative rather than in a limiting sense.

In general, the illustrated embodiments and aspects provide a device that couples an imaging system and a delivery system and/or minimally invasive interventional device. The delivery system can include, for example, delivery of materials to or from a target site or delivery of instruments and devices to a target site. In certain embodiments, the device can comprise a catheter that incorporates one or more variable frequency ultrasound transducers operating at one or more frequencies within the frequency range of 1-13 MHz. The imaging system guides and facilitates various procedures, thereby significantly assisting in the access of and performance of procedures on various organs, structures and body cavities within the body, particularly during minimally invasive procedures. Ultrasound provides particular benefits because it is biologically safe and uses non-radiating energy to provide detailed anatomic and, in some cases, functional images. The images generated by the present devices provide a user with direct vision within the body in real time. Further, ultrasound provides a user with visualization of structures as well as within and beyond structures. The described devices and methods are compatible with all surgical and diagnostic devices and will allow bedside emergency procedures.

The described devices and methods are suitable for use in a variety of medical procedures and, depending on the type of procedure, can be suitably designed and adapted for such use. In certain embodiments, the device can be in the form of any conventional catheters including, for example, biopsy catheters, ablation catheters, and mapping catheters. In certain embodiments, the present devices can be in the form of interventional devices (e.g. syringe, forceps, biopsy instruments, clamps, retractors, etc.) and/or are compatible with catheters, for example, biopsy catheters, ablation catheters, mapping catheters, and sheaths. In certain embodiments, the devices can be compatible with, for example, videoscopes and delivery needles such as those used for stem cell therapy.

Referring now to the various figures of the drawing wherein like reference characters refer to like parts, FIGS. 1-2 and 4-8 depict various views of a minimally invasive device 100 one or more embodiments. Devices for performing minimally invasive procedures, including sheaths (e.g., vascular sheaths), catheters, and interventional devices (e.g. forceps, biopsy instruments, clamps, retractors, etc.) are conventional in various forms as described above and, thus, although described and shown with reference to preferred embodiments, the general features (e.g. size, shape, materials) of the a device 100 may be in accordance with conventional devices.

Figure 1B:
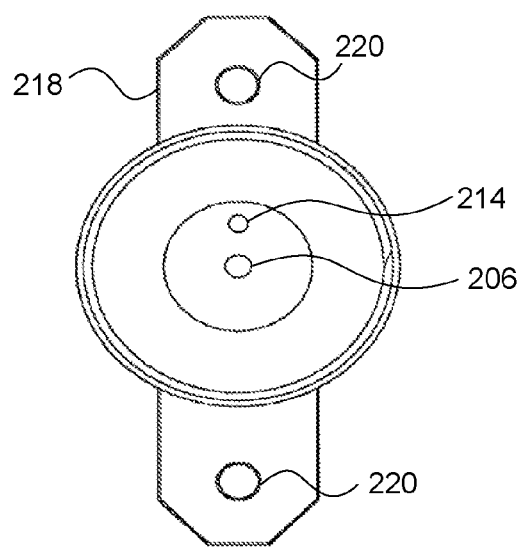
Figure 1C:
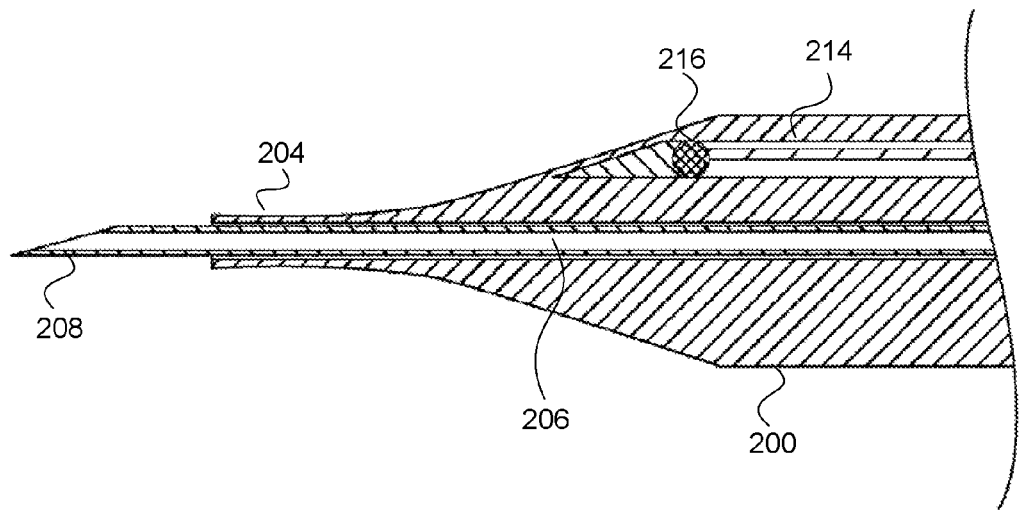
Figure 2:
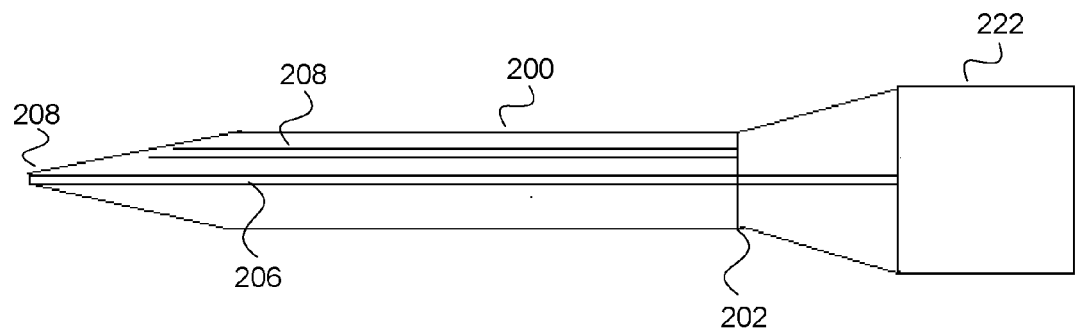
FIG. 2 shows a side cross-sectional view of the device of FIG. 1 without a needle housed within the device lumen.
Figure 3A:
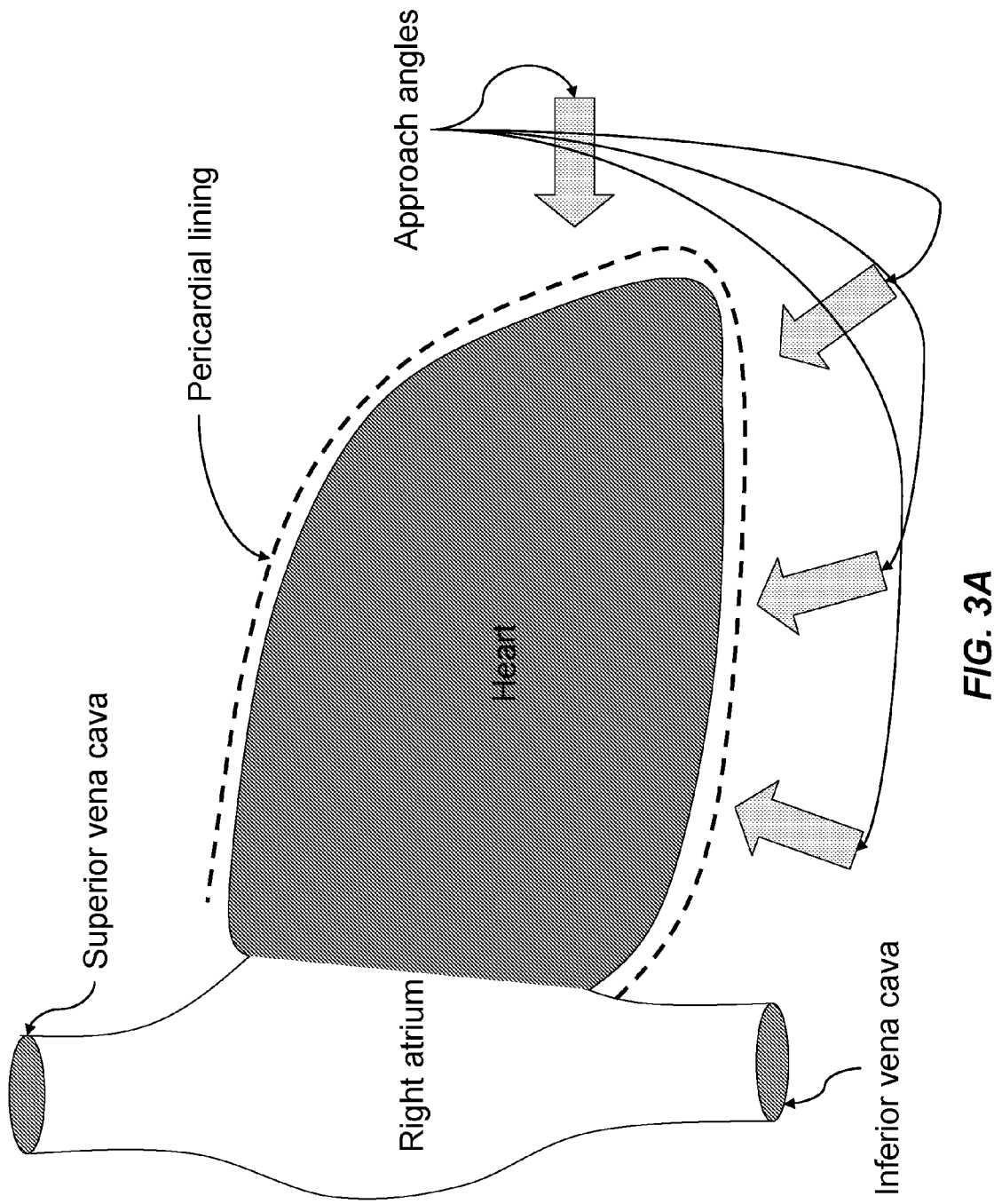
FIGS. 3A-G illustrate an embodiment wherein a device according to aspects herein can be used to access and perform a procedure in the pericardial space of a human body.
Figure 3B:
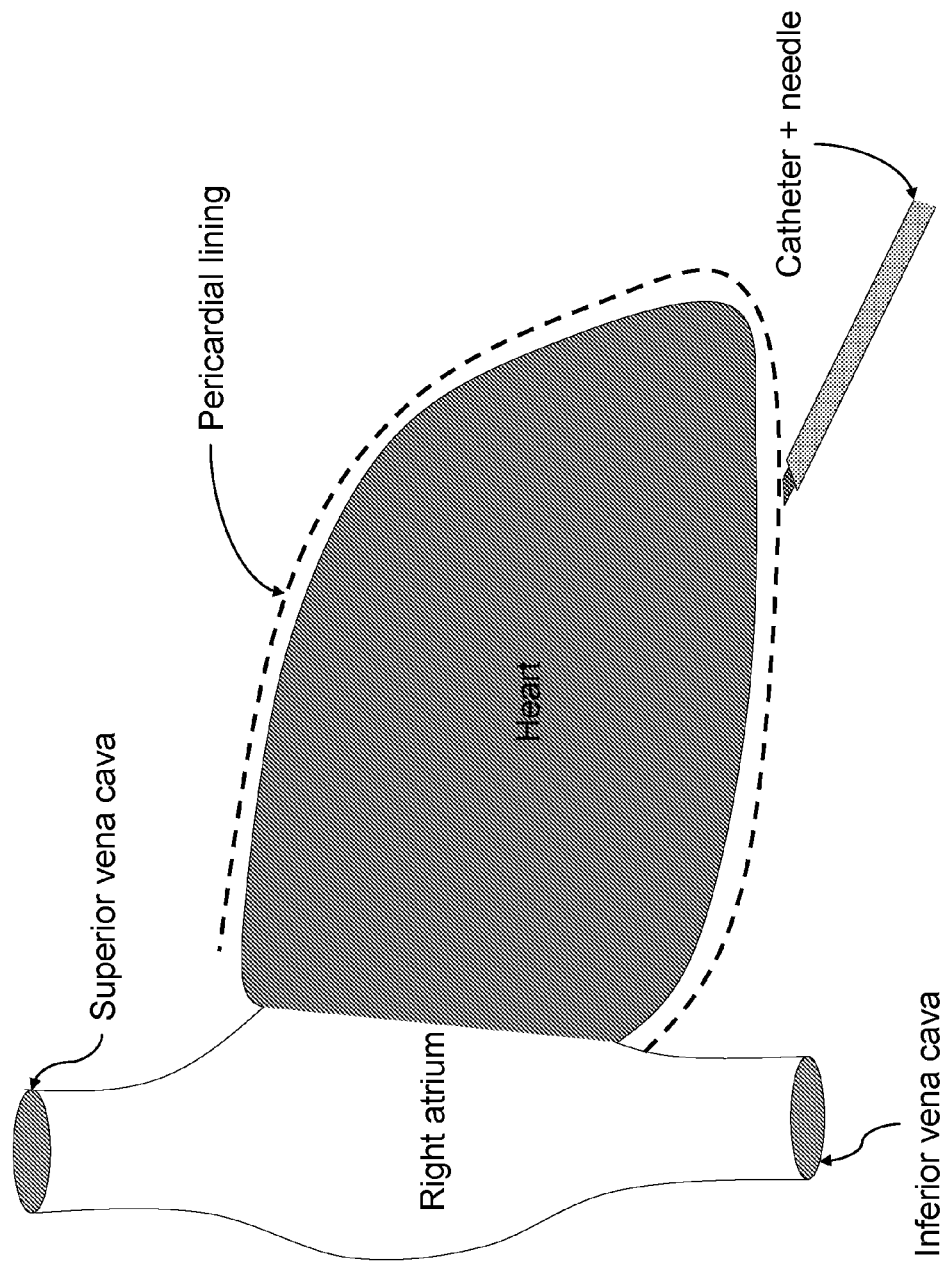
Figure 3C:
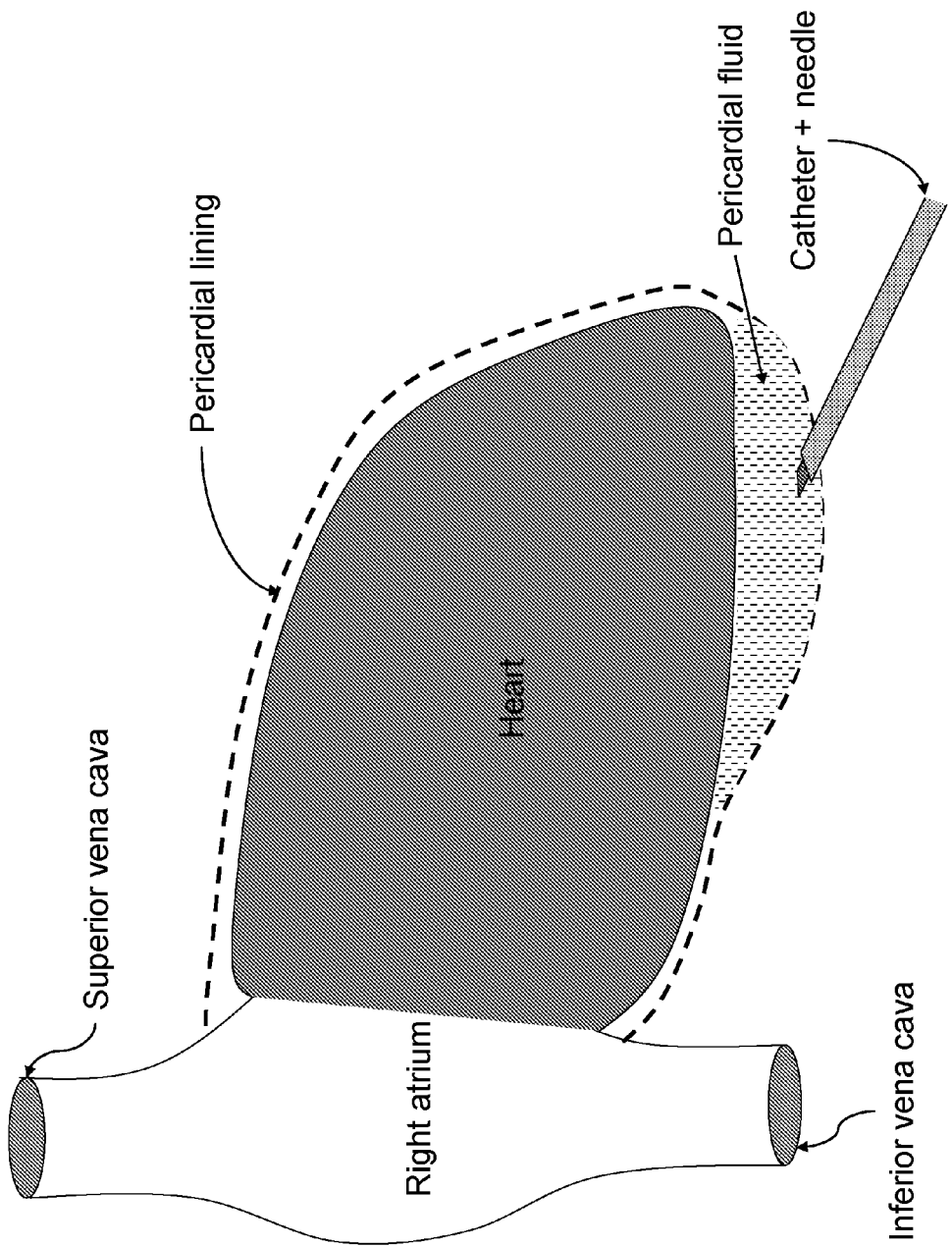
Figure 3D:
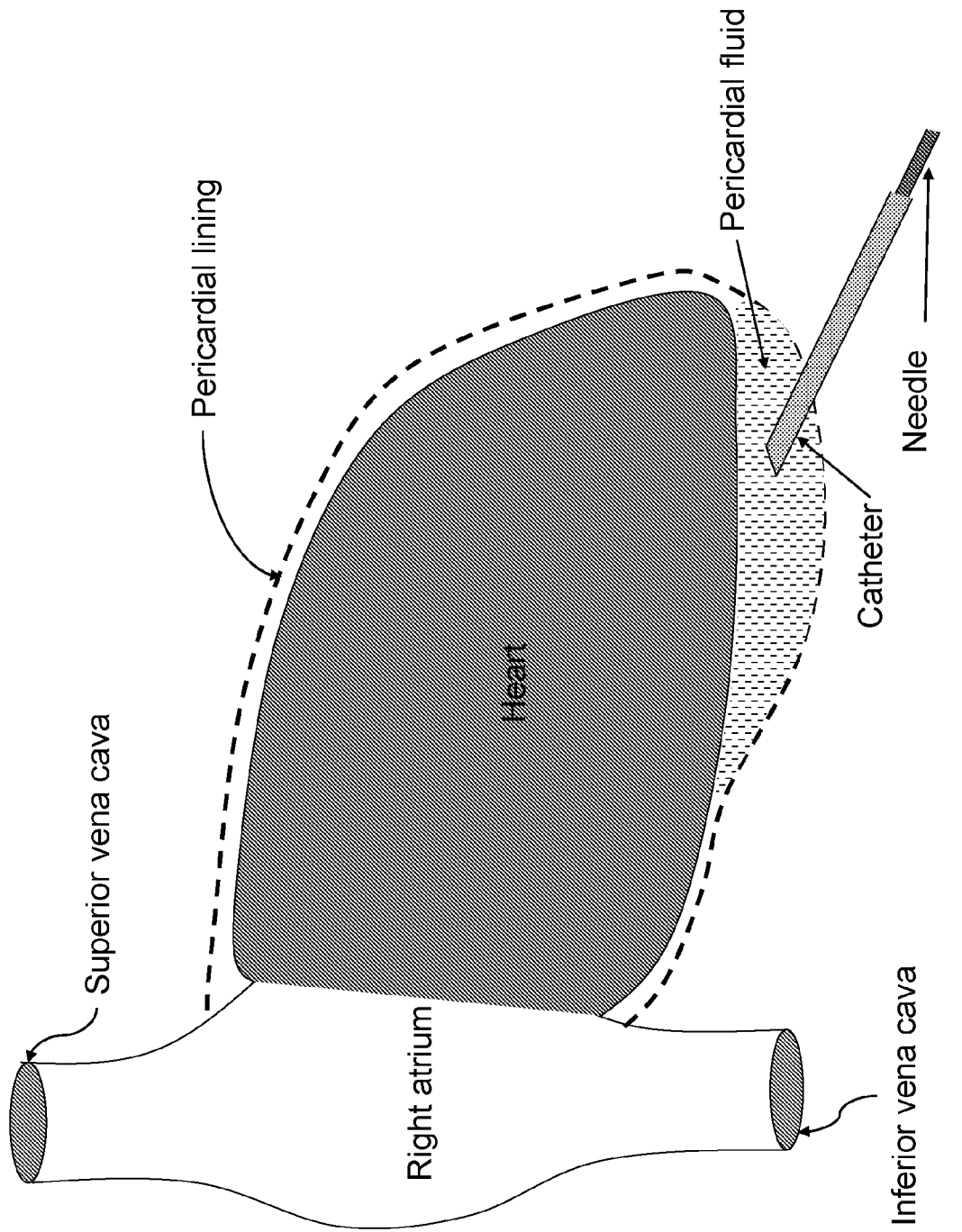
Figure 3E:
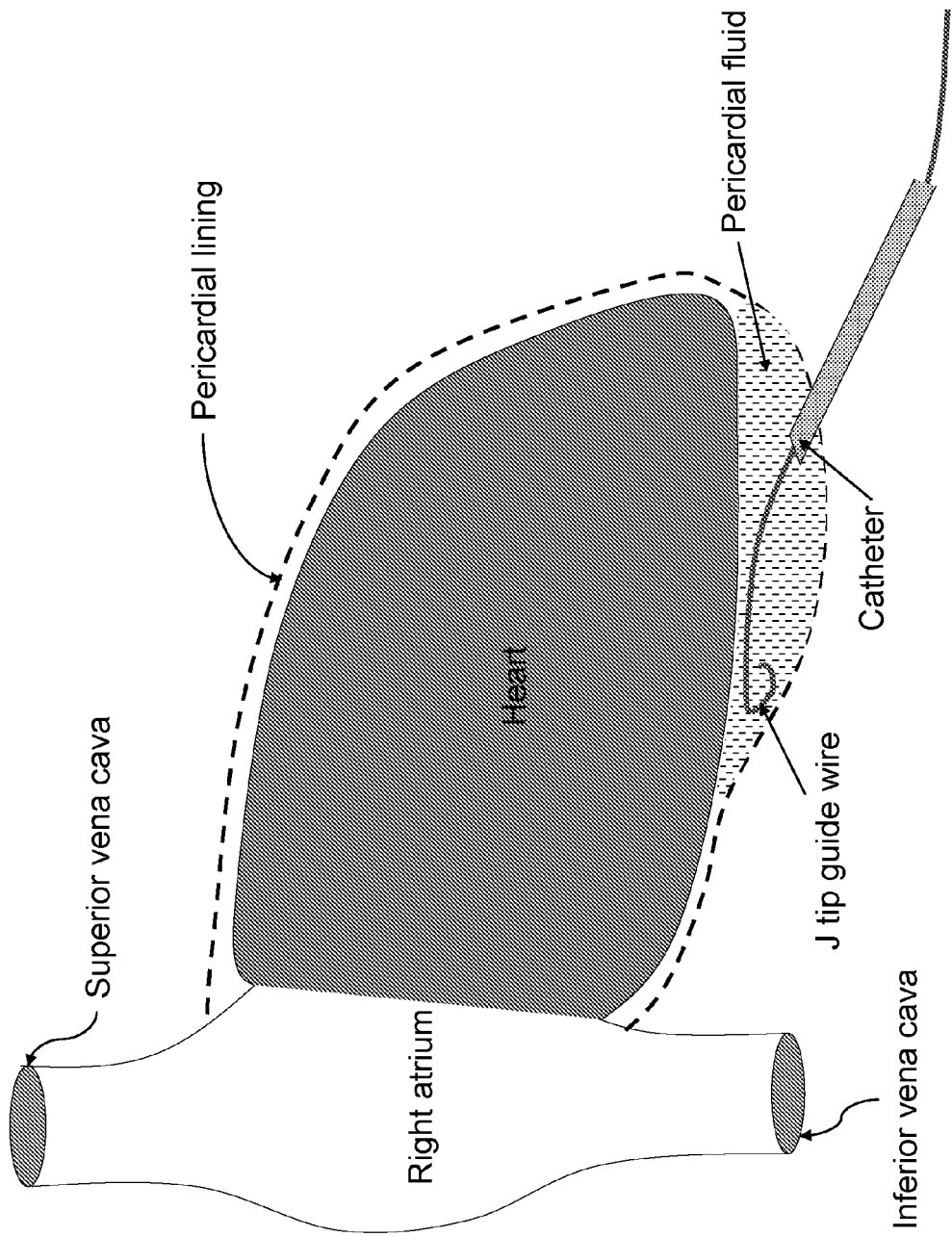
Figure 3F:
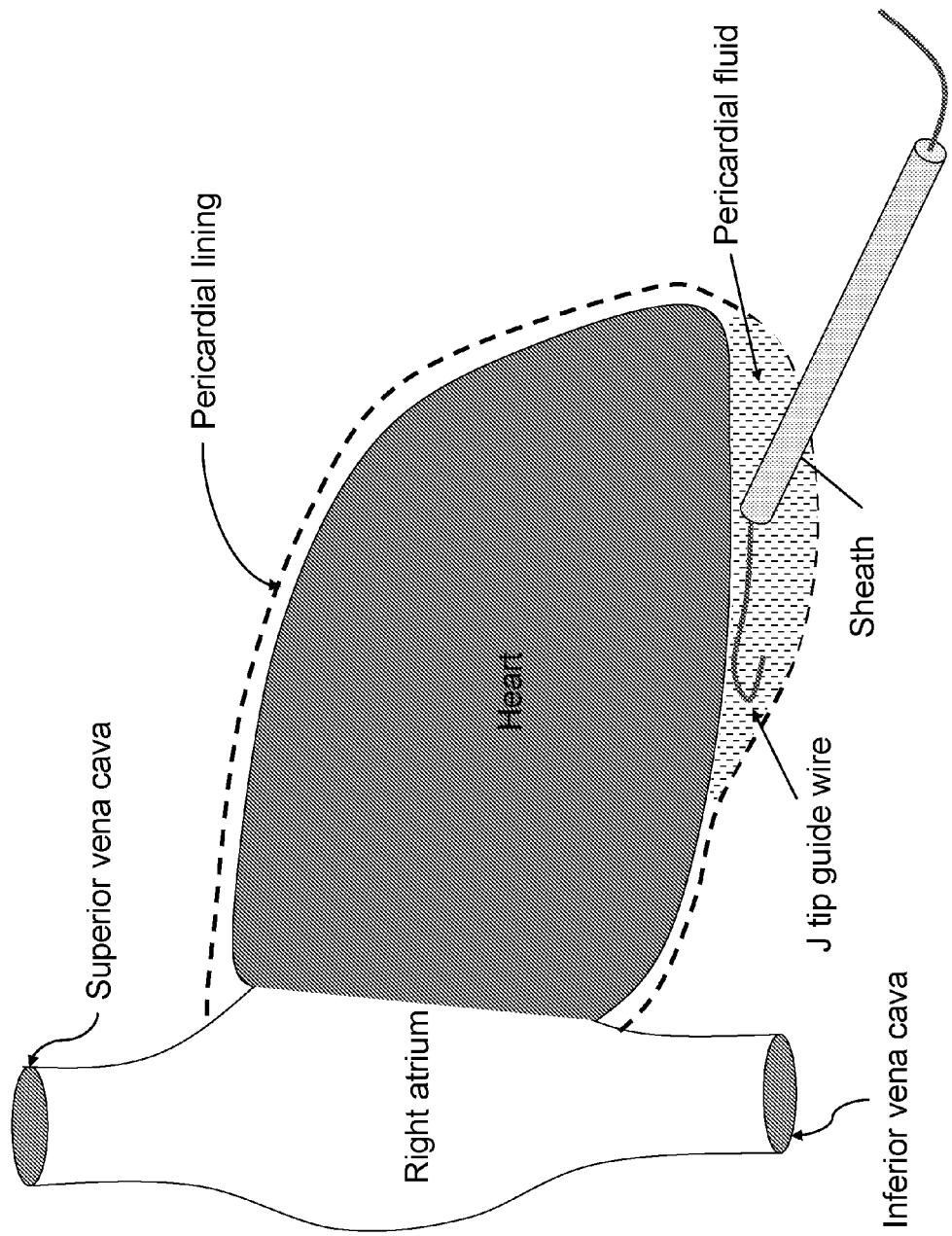
Figure 3G:
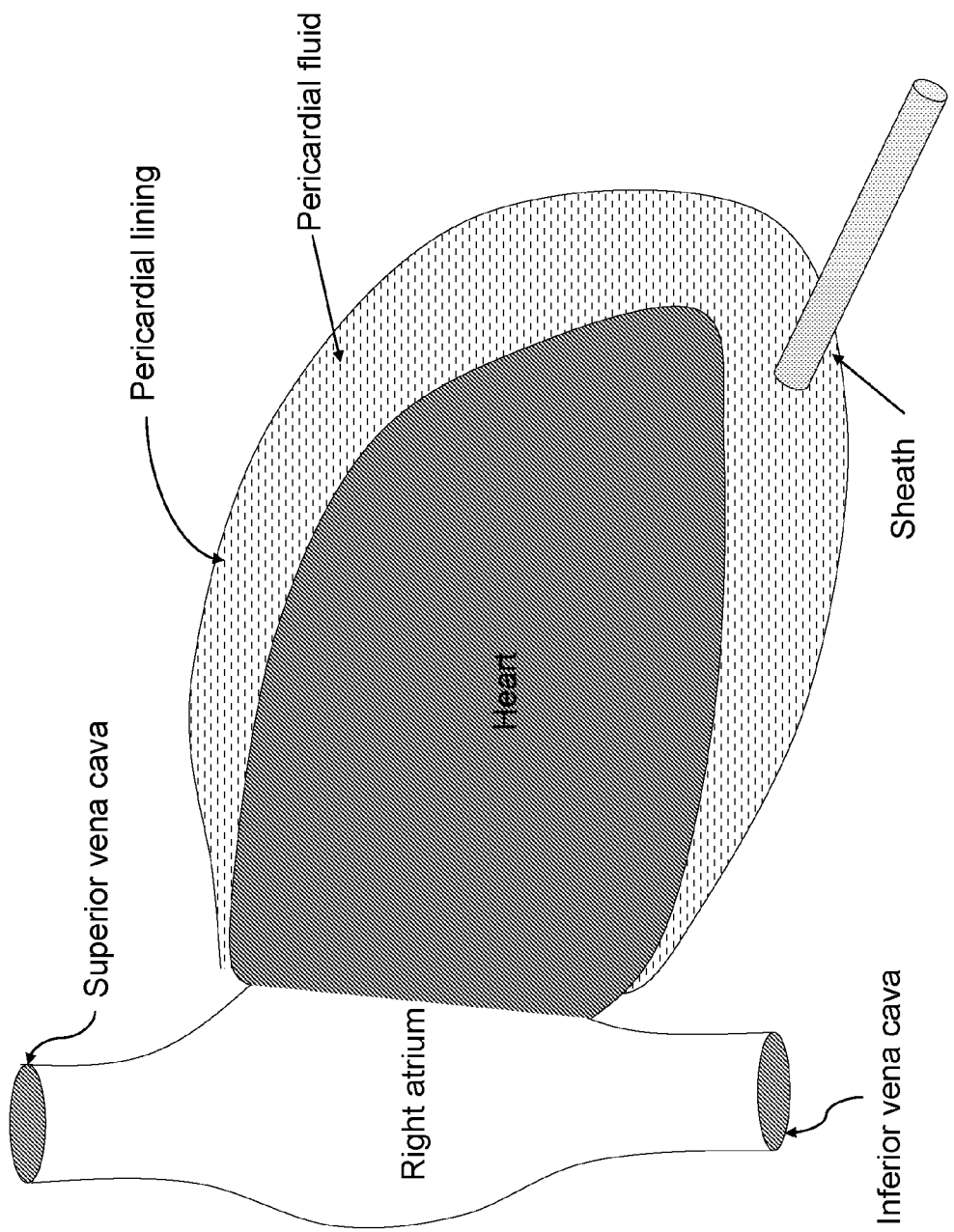

As shown in FIGS. 1 and 2, in one embodiment, the device 100 is in the form of a catheter and comprises an elongate body 200 having a proximal end 202 and a distal end 204. (In accordance with conventional practice, "proximal end" designates herein the specified end closest to the medical personnel manipulating the device, and "distal end" designates herein the opposite end placed within a patient).

The elongate body 200 can be fabricated of any conventional materials used in forming catheters, sheaths, and interventional devices. For example, when in the form of a catheter, the elongate body 200 can be fabricated of, for example, silicone, Teflon, polyurethane, PVC, or elastomeric hydrogel, for example, AQUAVENE®. In certain embodiments, the elongate body 200 is cylindrical in shape.

The dimensions of the elongate body 200 are not particularly limited and can vary depending on the ultimate use of the device 100, the insertion point, and the distance to the target area from the insertion point. For example, the outer diameter of the elongate body 200 can be limited by the size of an anatomical structure that it is to be inserted in. The outer diameter of the elongate body 200 can also be limited based on the desired size of the incision through which the device 100 is inserted and which must subsequently be closed. For example, when the device 100 is in the form of a vascular sheath, the outer diameter can vary depending on the targeted blood vessel through which the elongate body 200 is inserted. Such devices, when in the form of vascular sheaths used during cardiac procedures, can be inserted through a blood vessel in the upper thigh or, alternatively, can be inserted through a blood vessel in the arm. For example, in one embodiment, the device 100 can be inserted by anesthetizing an area the patient's upper thigh and inserting the elongate body 200 through a blood vessel in the upper thigh and towards the heart. In this embodiment, the elongate body 200 can have a length sufficient to traverse this pathway. The device 100 can also be in the form of a sheath used during a laparoscopic procedure, and in such a case, the elongate body 200 can generally have an outer diameter in accordance with conventional laparoscopic sheaths and will have a length that provides access to the target site. Further, the device can be used as a minimally invasive conduit from the skin surface to the target site to allow passages of catheters, guide wires, and instruments through elongate body 200, can the elongate body 200 can be sized to allow these various instruments to be passed therethrough.

In an exemplary embodiment, the device 100 can be in the form of a catheter that can be introduced through the chest to access various internal structures using minimally invasive techniques. As such, the elongate body 200 can have an outer diameter ranging from about 1 F to 15 F (wherein 1 F=0.33 mm) and a length ranging from about 1" to 20". Specific lengths and diameters can be provided based on the insertion site of the catheter, the distance to the desired target site(s), and the space required for insertion of one or more interventional devices through the elongate body 200.

In other embodiments, the device 100 can be in the form of any interventional device that can be, for example, inserted through a sheath or catheter to access various internal structures using minimally invasive techniques. As such, the elongate body 200 can have an outer diameter sized so as to fit within conventional sheaths or catheters, and a length suitable to access the desired target site(s) through the sheaths or catheters.

In certain embodiments, such as those seen in FIGS. 1, 2, and 7, the device 100 can be in the form of a catheter or sheath and the elongate body 200 is provided with one or more lumen 206 extending therethrough. Depending on the use of the lumen 206, the design and configuration can vary. For example, in some embodiments as described further herein, a central wire lumen 206a can be provided through which a needle 208 is insertable (e.g., a lumen 206a running along the center of the elongate body 200 as shown in, for example, FIGS. 1, 2, and 7A). The needle can be used, for example, to puncture various target sites and inject or withdraw materials from a target site. As such, the lumen 206 can be, for example, at least 8-30 gauge so as to accommodate an 8-30 gauge needle 208. Of course, the central wire lumen 206a can be provided in other sizes to accommodate other sizes of needles 208. In some embodiments, the device 100 can be provided with one or more interventional device lumen 206b (for example, as shown in FIG. 7B) through which one or more interventional devices can be inserted and manipulated. As such, these lumen 206b can be sized so as to allow for insertion and manipulation of interventional devices therethrough. In some embodiments, the device 100 can be provided with one or more injection/aspiration lumen 206c (for example, as shown in FIG. 7C) through which materials can be injected and removed. For example, emboli, blood clots and other materials can be evacuated from a blood vessel using an aspiration technique, and agents, such as medicaments, anticoagulants and contrast media may be injected into the treatment site using, for example, a syringe in connection with the lumen 206c. As such, these lumen 206c can be sized in accordance with conventional injection/aspiration lumen 206c. In some embodiments, a guidewire lumen 206d (for example, as shown in FIG. 7D) can be provided through which a guidewire is inserted for steerable guidance of the device 100 into the desired site. As such, the lumen 206d can be sized to accommodate conventional guidewires. In some embodiments, the device 100 is provided with any combination of these lumen 206a, 206b, 206c, 206d. Further, in some embodiments the lumen 206a, 206b, 206c, 206d can be used interchangeably. For example, in one embodiment, three lumen 206 are provided and can be used to insert, for example, a fiber optic endoscope, a biopsy needle, and a therapy delivery needle. In some embodiments, up to five lumen 206 are provided, each having independent entry ports (not shown) for insertion and deployment of up to 5 independent medical devices and/or injection/aspiration through the device simultaneously or individually.

Figure 6A:
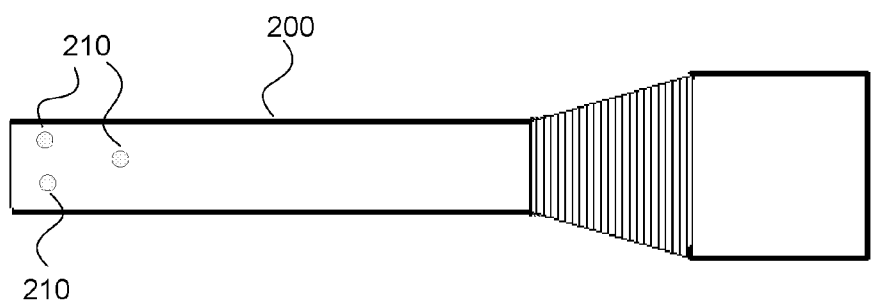
FIGS. 6A-C show side and cross-sectional views of embodiments of devices having different types of distal ends and various configurations of ultrasound transducers in accordance with one or more aspects.

As shown in FIGS. 1, 2, 6B, and 6C, the elongate body member 200 can be tapered at the distal end 204. This shape is particularly suitable for use in, for example, accessing the heart through the chest through the pericardium. However, the distal end can also be provided with other shapes such as, for example, rounded (e.g., as shown in FIG. 6A), square, beveled/angled, or pigtailed. Also, in some embodiments, the tip can be angled or beveled at an angle, such as an angle of 10°, 20°, 30°, 40°, 50°, 60°, 70°, or 90° as may be suitable for use in certain procedures.

Figure 7A:
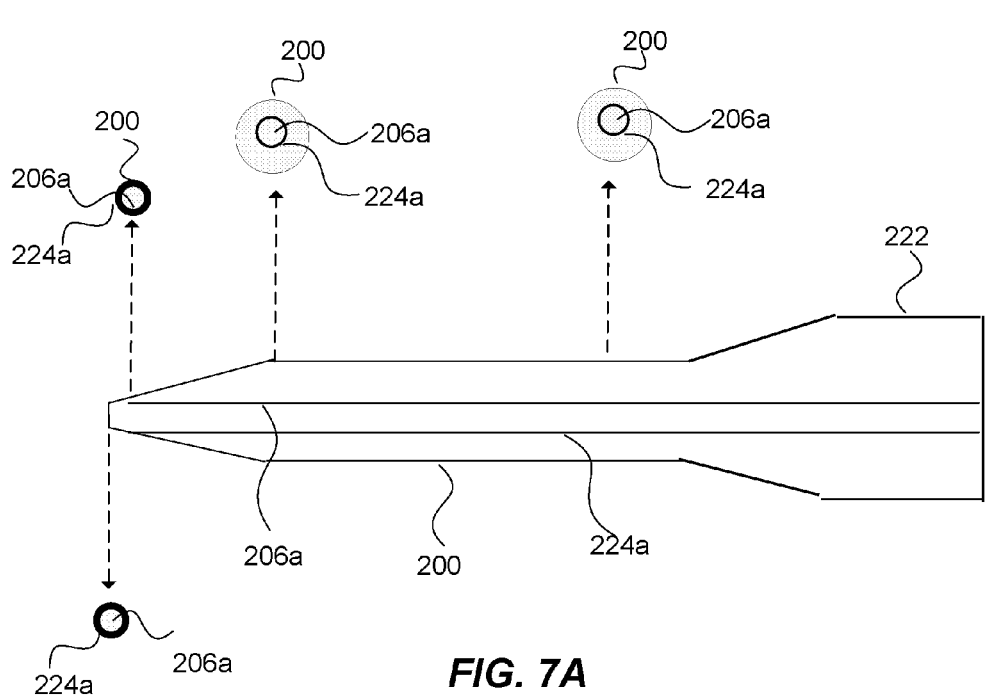
FIGS. 7A-D show side and cross-sectional views of devices having various types of lumen positioned in various arrangements.
Figure 7B:
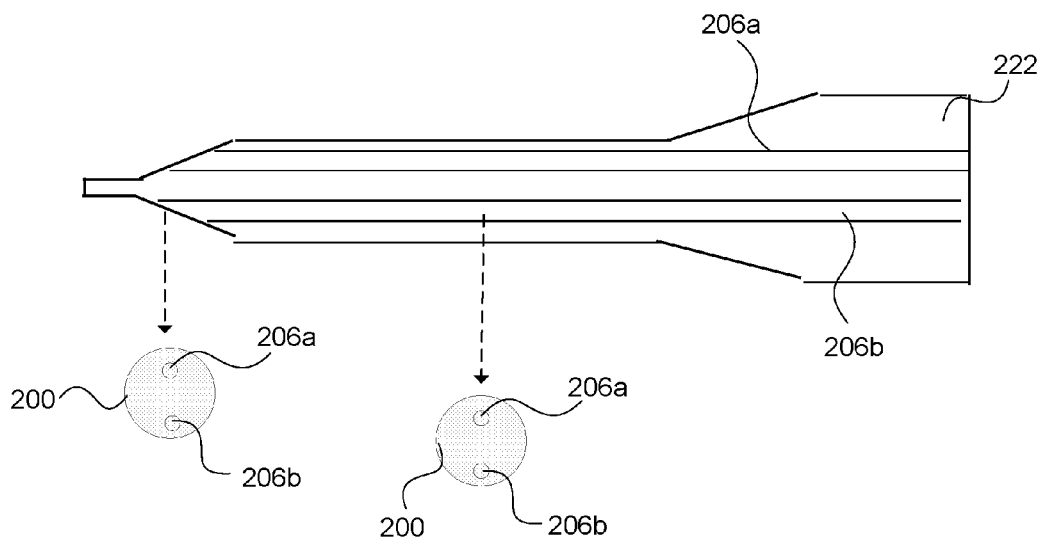
Figure 7C:
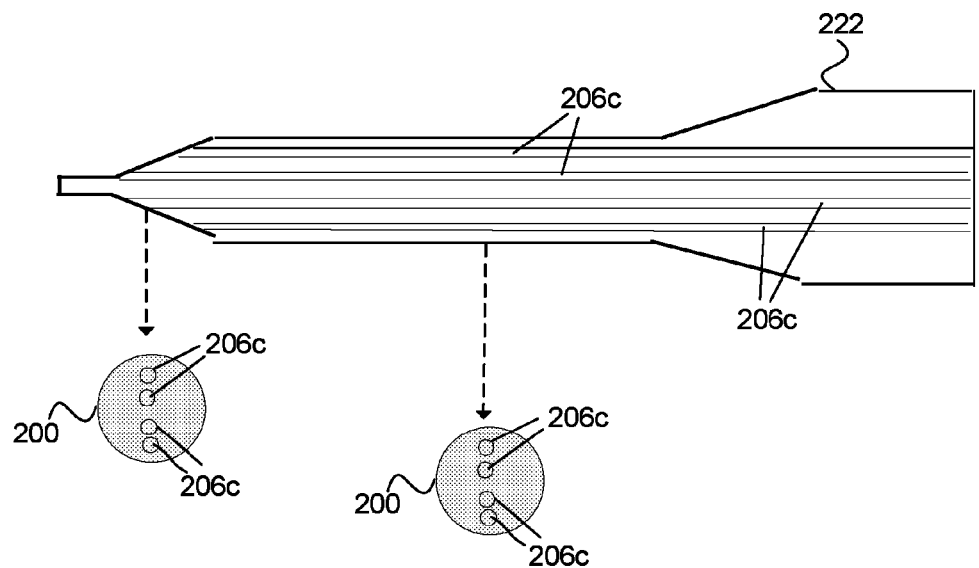
Figure 7D:
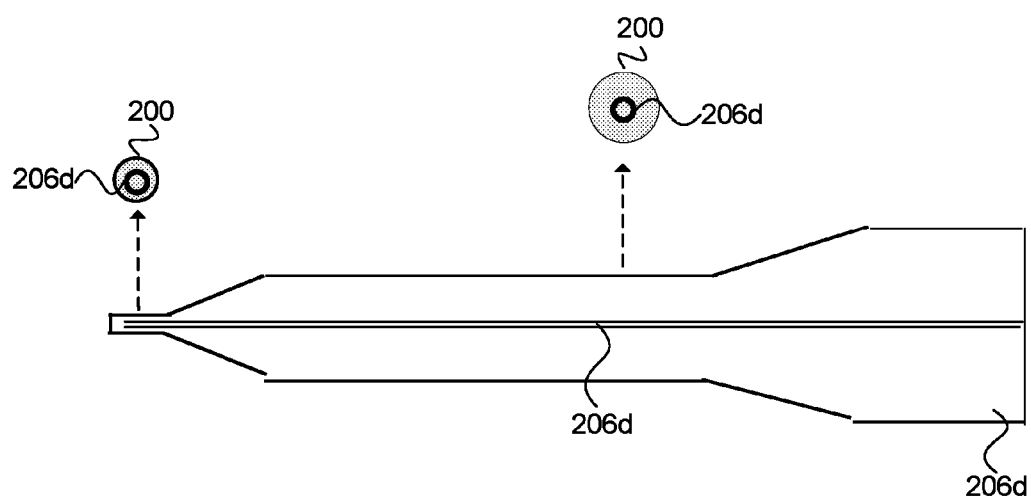
Figure 8A:
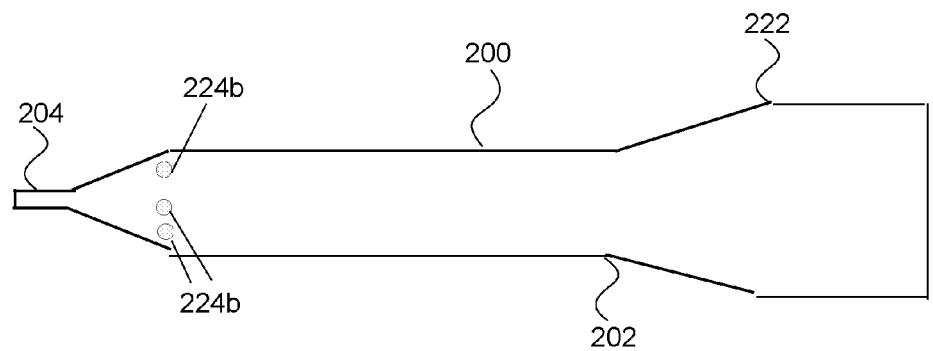
FIGS. 8A-B show side and cross-sectional views of devices having a plurality of ports positioned in various arrangements.
Figure 8B:
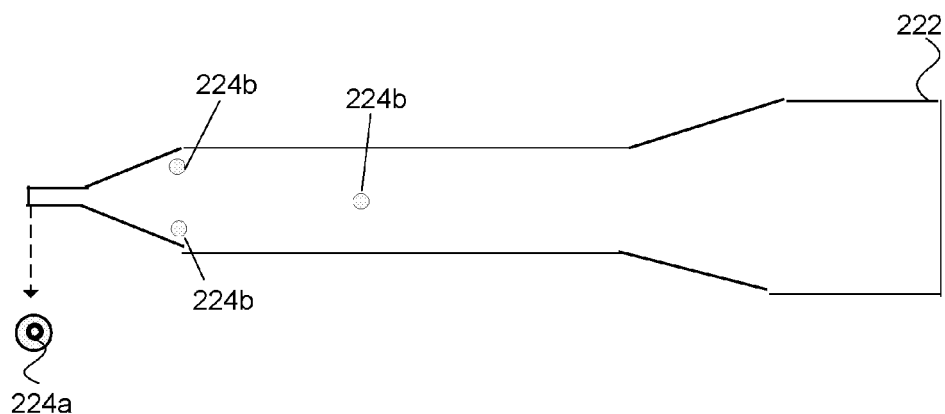

As seen in, for example, FIGS. 7A, 8A, and 8B, the distal end 202 of the body member 200 can be provided with one or more apertures 224 in connection with the one or more lumen 206. For example, one or more end apertures 224a can be located at the distal tip of the body member 200. In some embodiments, a central end aperture 224a can be positioned at the center of the distal tip of the body member 200, as shown in FIG. 7A. In some embodiments, a plurality of side apertures 224b can be provided in the walls of the elongate body 200 (for example, as shown in FIG. 8A). A combination of one or more end apertures 224a and one or more side apertures 224b can be provided (for example, as shown in FIG. 8B). In some embodiments, many side apertures 224b can be provided. The one or more of the apertures 224 can be provided with the same or varying diameters. The apertures 224, in connection with one or more lumen 206, can be used for injection and withdrawal of materials and insertion of various instruments (needles, guide wires, biopsy devices, etc.) In some embodiments, each aperture 224 can be in connection with its own lumen 206. In other embodiments, one or more apertures 224 can share a one or more common lumen 206.

In some embodiments, a luer lock 222 can be further provided at the proximal end 202 of the elongate body member 200. The luer lock 222 can be used to connect the device to, for example, a Touhey needle or a syringe (not shown). In some embodiments, a hemostatic valve and/or silicone pinch valve or water tight valve (not shown) can be located at the proximal end 202 of the elongate body 200 to prevent leakage of materials, such as blood and body fluids, out of the device 100. In some embodiments, a side-arm (not shown) in fluid communication with one or more lumen 206 may also be located near the proximal end 202 of the elongate body 200. An aspiration device or syringe can be connected to the side arm, if desired, to aspirate blood clot and other materials through the lumen 206 or to inject water, saline, contrast agent or similar material may be injected through the device 100 to a target site.

The device 100 incorporates an imaging system that provides a user with visualization within the body during a procedure. The imaging system is particularly useful in minimally invasive procedures wherein direct visualization of the target site is unavailable. In one embodiment, the imaging system can be in the form of an ultrasound system. Ultrasound systems are well-known and, thus, although described and shown herein with reference to one embodiment, the general features and components of the ultrasound systems may be varied in accordance with conventional systems.

Figure 6B:
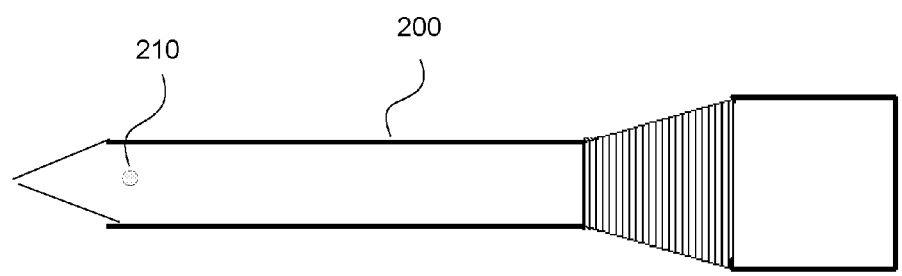
Figure 6C:
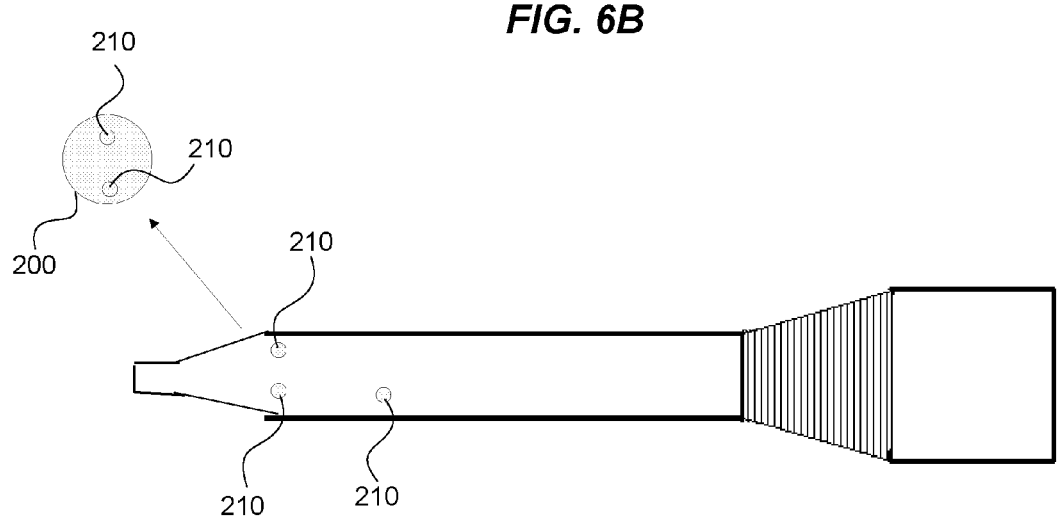

As shown in FIG. 1, the imaging system can include one or more ultrasound transducers 210 that are positioned on the elongate body 200. In some embodiments, one or more transducers 210 can be positioned at the distal end 204 of the elongate body 200 to provide imaging to a user as the device is guided to a treatment site such that, when the device is properly inserted and positioned at the target site, one or more transducers 210 can provide images of the target site. Alternatively, in some embodiments, one or more transducers 210 can be provided on one or more sides of the elongate body 200 along its length, either with or without a transducer positioned at the distal end 204. For example, as shown in FIGS. 6A-6C, any number of transducers 210 can be provided at any location along the elongate body member 200.

In general, a single transducer 210 is operated at any given time, although in some embodiments, a plurality of transducers 210, having different specifications as desired, can be provided on a device at various locations to provide a user with various imaging capabilities. For example, front-facing transducers can be provided in combination with side-facing transducers to provide a user with the capability to view structures in front of the device as well as to the sides of the device. Further, different sized and types of transducers can provide a user with various imaging capabilities (e.g. different sized views, more or less precision, etc.).

Transducers 210 can be in accordance with conventional transducers. For example, in some embodiments, the transducers 210 comprise piezoelectric materials such as PZT ceramics. The transducers 210 can also be of any size, with such size being limited by the size of the elongate body 200. As transducer size is decreased, the quality of the image provided also generally decreases. Thus, the smallest sized transducer that provides adequate imaging is generally used so as to minimize the required size required of the elongate body 200. For example 2-3 mm×2 mm transducers will generally require an elongate body of 5-6 Fr. In certain embodiments, the transducers 210 have a maximum dimension of 5 mm, in other embodiments 4 mm, in other embodiments 3 mm, and in other embodiments 2 mm.

The transducers 210 can generally be mounted or attached to the elongate body 200 by providing one or more mounting aperture (not shown) in which the transducers 210 can be fit and held by a friction. Various adhesives can further be used to hold the transducers 210 in place.

Figure 5:
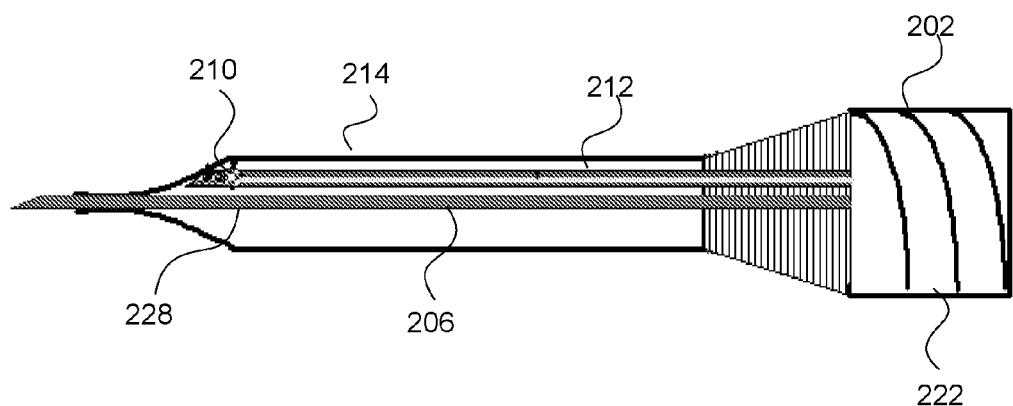
FIG. 5 shows a side view of another embodiment of a device in accordance with aspects herein.

For example, as seen in FIG. 5, conducting elements 212, which can control one or more transducers 210, can extend from the transducers 210 to the proximal end 202 of the elongate body 200 and can connect to an external system (ultrasound scanner) such as a gray scale color two-dimensional Doppler ultrasound system. Conducting elements 212 can cause the transducer to emit the sound waves and transmit sound waves reflected from tissues and structures to an ultrasound scanner where they can be transformed into a digital image. The conducting elements 212 can extend through the elongate body member 200 within one or more imaging lumen 214. The imaging lumen 214 can be provided in various sizes and, in exemplary embodiments, can range in size from 8-30 gauge.

To reduce ultrasound deflection during use of the device, the imaging system can be provided with matching layers 216 disposed adjacent, for example, adjacent the front face of the transducers 210 as shown, for example, in FIGS. 1A and 1C. The matching layers 216 can generally be in accordance with conventional matching layers and generally can include a matching layer front face and a matching layer rear face. The matching layers 216 can facilitate the matching of an impedance differential that may exist between the high impedance transducer elements and a low impedance patient. The matching layers 216 can generally be in accordance with conventional matching layers and can include a pocket with matching material that can reduce ultrasound deflection. Suitable matching layer materials can include, for example, plastic materials, such as polysulfone and REXOLITE® (a thermoset material produced by crosslinking polystyrene with divinyl benzene, available from C-LEC Plastics, Inc., Beverly, N.J.).

The imaging system may further include a backing layer (not shown) in accordance with conventional backing layers. The backing layers can generally be coupled to the rear face of the transducers 210 and function to attenuate acoustic energy that emerges from the rear face of the transducers 210. Generally, such backing layers can have a front face and a rear face, and can be fabricated of acoustic damping material that possesses high acoustic losses.

In some embodiments, as seen, for example, in FIG. 1B, the device 100 can further be provided with one or more anchoring portion 218 at the proximal end 202 of the elongate body member 200. The anchoring portion 218 can assist in maintaining the device 100 in proper position during use and can prevent or inhibit unwanted motion of the device. If desired, one or more sutures (not shown) can be used with the anchoring portion 218 for suturing the device to the skin to provide additional stability of the device during use. For example, the anchoring portion 218 can be provided with one or more suture holes 220.

In applications where the device 100 is inserted and guided through a blood vessel towards a target site, one or more guidewires (not shown) may further be incorporated into the elongate body 200 for steerable guidance of the device 100 into the pulmonary veins.

In some embodiments, the device 100 can be steerable and externally controlled. For example, the distal end 204 of the elongate body 200 can be manipulated by controls located on a portion of the device 100 positioned outside of the body during use. In some embodiments, one or more Micro-Electro-Mechanical Systems (MEMS) can be mounted on the device 100 at proximal and/or distal portions. MEMS systems include, for example, mechanical elements (beams, cantilevers, diaphragms, valves, plates, and switches), sensors, actuators, and electronics. MEMS also can be provided to function as tiny sensors and actuators. For example, MEMS can be incorporated in the device for measuring and monitoring pressure in the stomach or other organs in which the catheter is inserted, and for measuring and monitoring blood pressure when performing cardiac catheterization.

Figure 4:
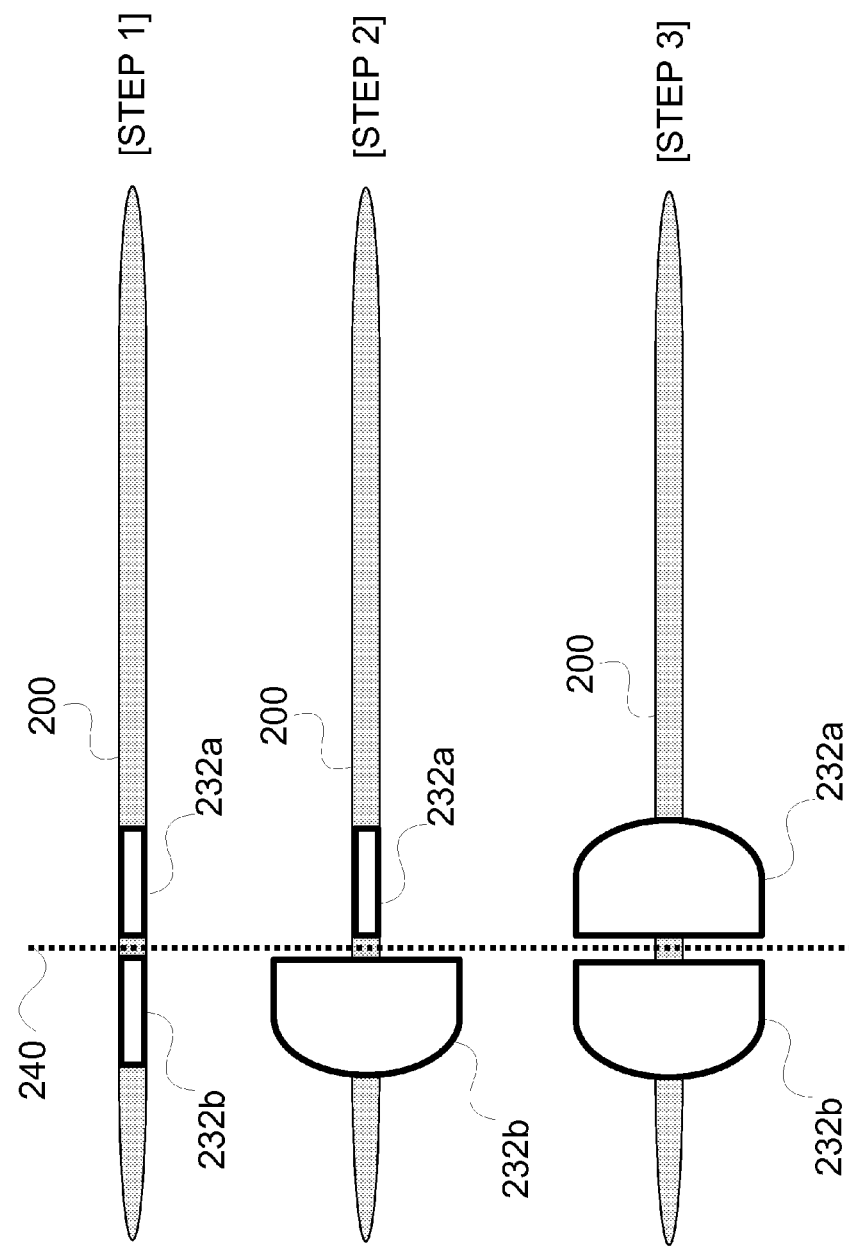
FIGS. 4A-C show side views of another embodiment of a device in accordance with aspects herein incorporating a pair of inflatable balloons for locating the device within an inner wall of a human body.

In some embodiments, as shown in FIG. 4, the device 100 can further incorporate one or more inflatable balloons 232 at the distal end 204 of the elongate body 200. In an exemplary embodiment, one or more balloons can be positioned approximately 2-10 cm from the tip of the catheter. In one embodiment, one or more ports (not shown) can be in connection with the balloons 232 via balloon inflation lumen (not shown) for infusion and removal of inflation material (e.g., saline). For example, ports can be provided in a hub (not shown) positioned at the proximal end of the device. One or more valves (not shown) can be provided at the ports or within inflation lumen to prevent unintentional withdrawal or leakage of material from the balloons 232. In one embodiment, for example, as shown in FIGS. 4A-C, two balloons, a proximal balloon 232a and a distal balloon 232b, can be provided. When used for pericardial procedures, the elongate body 200 is advanced intrapericardially using the incorporated ultrasound system for guidance. Once the distal balloon 232b is positioned intrapericardially, it is inflated and the elongate body 200 can be pulled back until the distal balloon 232b engages the inner surface of the pericardial wall 240. The proximal balloon 232a can then be inflated so as to engage the outer surface of the pericardial wall 240. In this manner, the pericardial wall 240 can be sandwiched between the proximal and distal balloons 232a, 232b to provide a relatively water-tight junction at the entry sight into the pericardium. Injection of fluids into the pericardium can be relatively leak-free as compared to injection without the use of the balloons. The general features of the balloons 232 can be in accordance with conventional inflatable balloons. Any conventional materials used in forming balloons for medical and surgical procedures can be used such as, for example, silicone and Teflon. In general, the balloons should be able to withstand about 3 atm pressure. The balloons can be inflatable using any materials conventionally used to inflate such balloons including, for example, saline. In another embodiment in accordance with aspects herein, a luer lock syringe can be provided for connection with luer lock 222. The luer lock syringe can be fastened to the device 100 to provide for saline withdrawal, for example, at the end of the procedure prior to removal of the device 100 from the treatment site.

In certain embodiments, the device 100 can be adapted for use in biopsy procedures including, but not limited to myocardial biopsy, brain biopsy, muscle biopsy, lung biopsy, liver biopsy, kidney biopsy, uterine and ovarian biopsy, esophageal biopsy, stomach biopsy, intestinal biopsy, tumor biopsy (anywhere), targeted biopsy of potentially abnormal zones in any of the above items (e.g., ultrasound guided biopsy of an abnormal area in the liver or kidney with the present catheter will allow access to the abnormal area, identification of abnormal zones by deploying the ultrasound and biopsy instrument to the specific area of interest). As such, the device 100 can, in some cases, be in the form of a catheter or sheath-like device that is insertable through small incisions in the body. The sheath-like device could include one or more lumen through which a biopsy tool could be inserted. The device 100 in the form of a sheath could, thus, be provided along its length, as set forth above, with one or more ultrasound transducers 210 along with the other components required to provide ultrasound imaging using the transducers 210. In another case, the device 100 could, itself, be a biopsy tool (either a minimally invasive biopsy tool that is insertable through a sheath or a biopsy tool that is directly insertable within the body). In this embodiment, the distal portion of the biopsy tool could include the mechanism for obtaining a biopsy (tissue sample) as well as one or more transducers 210, along with the other components required to provide ultrasound imaging using the transducers 210 as discussed herein.

In some embodiments, the device 100 can be used, for example, as shown in FIGS. 3A-3G, to provide access to vascular structures including arteries, veins, lymphatics, and to other hollow structures such as the gastrointestinal tract, genitourinary tract, and the respiratory system. As such, the device can be in the form of, for example, a vascular sheath. Such sheaths are well known, and, thus, the general features of the device 100 for these embodiments can be in accordance with conventional devices. The device 100 could further include one or more transducers 210, along with other components used to provide ultrasound imaging using the transducers 210 as discussed herein.

In other embodiments, the device 100 can be used in procedures in various body spaces such as the pleural peritoneal space, pericardial space, perisphinal space, pelvis, and cerebrospinal space. For example, the device can be adapted for use in paracentesis, biopsy of any intra abdominal or intrapelvic organ, prostate biopsy, biopsy of tumors or otherwise suspected abnormal structures within the pelvis and abdomen, diagnosis of endometriosis, treatment by chemicals, cells, bio-agents, physical energy (e.g., cryo, radiofrequency, heat, laser) of any pathology within the pelvis and abdomen, visualization and application of therapy within the genitourinary tract, and drainage of abnormal or normal collection of fluid in actual or potential space in the abdomen, pelvis or genitourinary tract. The device 100 can be in the form of a catheter or sheath that provides entry into these various body spaces, thus allowing therapy delivery, intervention, placement of devices and diagnostics. The device 100 can also be in the form of interventional devices for use in procedures within these spaces. Such catheters, sheaths, and devices are well known, and, thus, the general features of the device 100 for these embodiments can be in accordance with conventional devices. The device 100 could further include one or more transducers 210, along with the other components required to provide ultrasound imaging using the transducers 210 as discussed herein. Procedures such as thoracentesis, ascites tap, biopsy of any organ, delivery of drugs or devices, can be made substantially safer and easier through the use of such devices by the imaging provided thereby In some embodiments, the device 100 can be designed for use in cardiac procedures and for accessing various targets such as, for example, epicardial biopsy, electronic mapping (endocardial or epicardial), electromechanical mapping (endocardial or epicardial), endocardial or epicardial ablation using any form of energy, canulation or delivery of catheters, pacing leads, and interventional devices, mapping and access to the fossa ovalis and patent foramen ovale to enable crossing the atrial septum and allowing transvenous access to the left side of the heart, access to structures such as the coronary sinus and other cardiac venous structures, epicardial electrical and electromechanical mapping and ablation using any form of energy, pericardiocentesis, left ventricular lead placement, delivery of therapy (e.g., drugs, stem cells, laser therapy, ultrasound energy), epicardial coronary artery bypass, valve repair and placement, delivery of cardiac shape modifying devices (e.g., for ACORN-like, MYOSPLINT), myocardial scar reconstruction, ventricular reconstruction, ventricular assist device placement, and the treatment by chemicals, cells, bio-agents, physical energy (e.g., cryo, radiofrequency, heat, laser) of any pathology within the pericardial space or myocardium or intracardiac. As such, the device 100 can, in some cases, be in the form of a sheath-like device that is insertable through, for example, an incision in the patient's upper thigh and through a blood vessel all the way up to the heart. In such embodiments, guidewire can be provided within the device. Alternatively, the device can be inserted through the pericardial space. The device 100, in the form of a sheath, could thus be provided along its length, as set forth above, with one or more ultrasound transducers 210 along with the other components required to provide ultrasound imaging using the transducers 210. In other embodiments, the device 100 can be in the form of a device that is used in performing the cardiac procedure (e.g. biopsy, or valve repair instruments) and can be provided with one or more transducers 210, along with the other components required to provide ultrasound imaging using the transducers 210 as discussed herein.

In other embodiments, the device 100 can be in the form of devices for use in performing procedures on the musculoskeletal system and for accessing the musculoskeletal system, such as, for example, the treatment by chemicals, cells, bio-agents, physical energy (cryo, radiofrequency, heat, laser) of any pathology within the joint cavity, joint components, or muscle and bone, visualization and application of therapy involving muscle, bone, and joint components, including joint cavity, and drainage of abnormal or normal collection of fluid in actual or potential space in the muscle, bone, or joint components. In these embodiments, the device 100 can be in the form of a catheter or sheath that provides access to the musculo-skeletal system, thus allowing therapy delivery, intervention, placement of devices and diagnostics. The device 100 can also be in the form of interventional devices for use in procedures on the musculo-skeletal system. Such catheters, sheaths, and devices are well known, and, thus, the general features of the device 100 for these embodiments can be in accordance with conventional devices. The device 100 can further include one or more transducers 210, along with the other components required to provide ultrasound imaging using the transducers 210 as discussed herein.

In some embodiments, the device 100 can be in the form of devices for use in procedures on the brain and nervous system and for accessing the brain and nervous system. For example, such devices can be used for the treatment by chemicals, cells, bioagents, physical energy (cryo, radiofrequency, heat, laser) of any pathology within the cranium and spinal and pen-spinal space including the vasculature contained within, visualization and application of therapy within the cranium, spinal, and peri-spinal space and all contained vasculature, drainage of abnormal or normal collection of fluid in actual or potential space in the cranium, spinal, and pen-spinal space and all contained vasculature, and for transcatheter delivery of interventional devices such as aneurysm clips, hematologic treatments, and any other drug or non drug therapy, either directly or via the vasculature or via any other hollow structure within the cranium, spinal, and peri-spinal space and all contained vasculature. In these embodiments, the device 100 can be in the form of a catheter or sheath that provides access to the brain and system, thus allowing therapy delivery, intervention, placement of devices and diagnostics. The device 100 can also be in the form of interventional devices for use in procedures on the brain and nervous system. Such catheters, sheaths, and devices are conventional, and, thus, the general features of the device 100 for these embodiments can be in accordance with conventional devices. The device 100 can further include one or more transducers 210, along with the other components required to provide ultrasound imaging using the transducers 210 as discussed herein.

In some embodiments, the device 100 can be in the form of devices suitable for use in procedures on the vasculature procedures and for providing access to the vasculature. For example, the devices can be adapted for visualization and application of therapy within the body vasculature and for the delivery of devices or drugs including stents, and any form of energy to the vasculature. In these embodiments, the device 100 can be in the form of a catheter or sheath that provides access to the body vasculature, thus allowing therapy delivery, intervention, placement of devices and diagnostics. The device 100 can also be in the form of interventional devices for use in procedures on the vasculature. Such catheters, sheaths, and devices are well known, and, thus, the general features of the device 100 for these embodiments can be in accordance with conventional devices. The device 100 could further include one or more transducers 210, along with the other components required to provide ultrasound imaging using the transducers 210 as discussed herein.

The device 100 can further be adapted for use in procedures on the nasal passages, sinuses, and pharynx and for accessing the nasal passages, sinuses, and pharynx. In these embodiments, the device 100 can be in the form of a catheter or sheath that provides access to a desired site of the nasal passages, sinuses, and pharynx, thus allowing therapy delivery, intervention, placement of devices and diagnostics. The device 100 can also be in the form of interventional devices for use in procedures on the nasal passages, sinuses, and pharynx (e.g., devices for therapy delivery, intervention, placement of devices and diagnostics). Such catheters, sheaths, and devices are well known, and, thus, the general features of the device 100 for these embodiments can be in accordance with conventional devices. The device 100 can further include one or more transducers 210, along with the other components required to provide ultrasound imaging using the transducers 210 as discussed herein.

The device 100 can further be in the form of devices used to treat and address chronic problems and, as such, can be delivered and lodged in body cavities, organs, or other anatomic locations for long term monitoring or anatomy or function or dynamics including hemodynamics. In these examples, the device can be in the form of a catheter or sheath or other conventional chronic treatment or monitoring device that can be lodged at a desired site. The device 100 can further include one or more transducers 210, along with the other components required to provide ultrasound imaging using the transducers 210 as discussed herein.

In some embodiments, the present device 100 can further be integrated with other non-ultrasound imaging modalities including infrared, laser, optical coherence, fiber optic instruments including, but not limited to endoscopic mapping. For example, the body member 200 can further be provided with a fiber optic lumen through which an optical fiber is insertable.

The present device 100 also can be used to provide a three-dimensional mapping system solely using the incorporated ultrasound system or in connection with other imaging modalities such as computed tomography, magnetic resonance, videoscopy. When the device is in the form of a catheter or sheath, this will allow stereotactic and remote/robotic operation of devices inserted and manipulated through the device 100. In such a system, an imaging modality (ultrasound, CT or MRI) can be used to generate a 3 dimensional image. The device will interactively use the generated images to be directed either manually or through an automated or semi-automated process for deployment to a target area displayed in the 3 dimensional image. The device 100 is generally used in connection with an ultrasound display system (B mode image or 3D image) that interfaces with the device to produce and display the images.

The devices 100 can be used to perform any variety of medical procedures including those set forth herein. The general features of these procedures is in accordance with conventional procedures and further make use of the integrated imaging system to provide visualization while accessing and performing procedures at the target site. For example, as discussed above, a device of the invention can be utilized to obtain biopsy or material (including) fluids for testing from various organs or fluid collection sites through such pericardial access, or other entry into a patient.

Other procedures can be performed using embodiments and aspects of the device 100 described herein. In one embodiment, the device 100 can be used to provide pericardial access and effusion of fluid from the pericardium. In general, imaging procedures, such as transthoracic imaging, can be used to confirm the location of desired effusion. The surgeon can then mark an optimal entry site on skin. The skin and subcutaneous tissue can be infiltrated with lidocaine or other agent, followed by a small stab incision on the skin. The device 100 can be inserted and advanced to the site. The device can be attached to a syringe (e.g., a 1-cc, 5-cc, 10-cc, 20-cc, 30-cc, 40-cc, 50-cc or larger syringe) before or after insertion and advancement. The device 100 can be used to provide ultrasound images as the device 100 is advanced to the pericardial lining. Using the images provided by the device, the pericardial lining can be punctured using the needle 208, and the surgeon can confirm backflow in the device/syringe. The elongate body 200 can be advanced, and the needle 208 removed. A guide wire can then be advanced to the site via a lumen 206. The body member 200 can be removed and a sheath advanced over guide wire. Pericardial fluid can then be drained to dry. Transthoracic ultrasound or ultrasound using the present device 100 can then be used to confirm proper drainage. In this regard, as discussed above, devices of the invention can be especially useful in loculated or compartmentalized effusions in the heart (pericardial), abdomen (ascites), chest, or abscesses in any organ or body cavity. The distal end imaging (particularly in real-time) can allow safe and accurate access to multiple compartments and ensure safe and complete drainage.

In another embodiment, the device 100 can be used to provide pericardial access without effusion, for example, as shown in the exemplary procedure illustrated in FIGS. 3A-3G. In general, imaging procedures, such as transthoracic imaging, can be used to confirm the location of the heart. The surgeon then can mark an optimal entry site on skin. The skin and subcutaneous tissue can be infiltrated with lidocaine, followed by a small stab incision on the skin. The device 100 can be inserted and advanced to the site. The device can be attached to a syringe (e.g., a 20 cc syringe loaded with saline and lidocaine or other agents) before or after insertion and advancement of the device 100 into the pericardium. The transducer 210 can be used to provide ultrasound images as the device 100 is advanced to the pericardial lining. Using the images provided by transducer 210, the pericardial lining can be punctured using the needle 208. The syringe contents can be injected through the needle into the pericardium. The position of the fluid can then be confirmed using the device's ultrasound system, and the elongate body 200 can be pushed, under guidance, into the pericardial space. Additional material from the syringe can be injected, if necessary, to create a safe "pericardial pocket". The needle 208 can be removed and a guide wire advanced via the device 100. The device 100 then can be removed and a sheath advanced over the guide wire. Saline (up to 100-150) can then be injected into the pericardium and the pericardium can be monitored with transthoracic ultrasound or ultrasound using the present device. Interventional and/or diagnostic devices can then be advanced through the sheath. The planned procedure can then be performed and pericardial fluid aspirated as necessary. The sheath can then be removed and the incision closed with, for example, TEGADERM® dressing or STERISTRIPS®

Such access to the pericardial space then can permit a variety of discussed procedures including e.g., epicardial mapping, lead placement, intracardiac interventions, and the like.

Access to other organs, structures, and spaces can be performed in similar fashion with appropriate procedural modifications specific for the particular organs, structures or spaces.

All documents mentioned herein are incorporated by reference herein in their entirety.

Although the instruments and methods discussed above and primarily illustrated and described herein provide instruments that also can be adapted for performing laparoscopic radical prostatectomy on humans, it will be appreciated by those skilled in the art that such instruments and methods also are adaptable for use in other particularly delicate surgical procedures (both open and laparoscopic) as well as in performing various veterinary surgeries. Further, while the instruments and methods are primarily illustrated and described in connection with clamps and dissectors, other instruments (e.g. various laparoscopic and open surgery instruments such as graspers, scissors, forceps, biopsy punch, biopsy spoon, and hooks) could likewise be provided as described herein. Further, while several preferred embodiments have been described using specific terms, such description is for illustrative purposes only, and it is to be understood that changes and variations may be made without departing from the spirit or scope of the following claims.

I claim:

1. An interventional medical device for pericardial access configured to perform minimally invasive surgical procedures comprising at least one ultrasound transducer, the device comprising
    an elongate body having no exterior delivery catheter or sheath configured to facilitate entry of a catheter through skin tissue of a human body, the elongate body configured to be introduced directly through a chest of the human body to the pericardium after a small stab incision on the skin during use of the device, the elongate body having proximal and distal ends, the elongate body having a tapered tip at the distal end, the elongate body configured to be a conduit from a skin surface of the chest to a target site proximate the pericardium during use of the device;
    an insertable needle configured to puncture an internal wall of the human body proximate the target site during use of the device;
    a plurality of lumen extending through the elongate body, one lumen extending through the elongate body having an end aperture at a distal tip of the tapered tip of the elongate body, the one lumen adapted to receive the insertable needle during use of the device, the insertable needle configured to puncture the target site as the needle extends from the end aperture during use of the device;
    said at least one ultrasound transducer being located at an outer periphery of the tapered tip of the elongate body and proximally located near the distal end in relation to the end aperture and oriented and configured to provide images for guidance of movement of the elongate body from the chest to the target site proximate the pericardium of the human body and images of said needle puncture of the human body wall during use of the device; and
    an anchoring portion near the proximal end of the elongate body for maintaining a proper position during use of the device.

2. The interventional medical device as recited in claim 1, said anchoring portion having at least one suture hole.

3. The interventional medical device as recited in claim 1, further comprising a luer lock at the proximal end of the elongate body for coupling a syringe to the insertable needle configured to puncture a pericardial lining of the pericardium during use of the device, the insertable needle extending through the one lumen having the end aperture at the distal tip to the distal end during use of the device.

4. The interventional medical device as recited in claim 1, further comprising a micro-electro-mechanical system mounted on the device configured to monitor pressure within a human body during use of the device.

5. The interventional medical device as recited in claim 1, the elongate body further comprising first and second inflatable balloons configured to provide, when inflated, a stationary grasp of an inner wall of a human body during use of the device, the balloons configured to sandwich said inner wall during use of the device.

6. The interventional medical device as recited in claim 1, comprising first and second imaging lumen, a first imaging lumen for ultrasonic imaging and a second imaging lumen for fiber optic imaging.

7. The interventional medical device as recited in claim 1, further comprising at least one side aperture of the elongate body corresponding to a lumen configured for delivery to a human body during use of the device in the vicinity of said side aperture.

8. The interventional medical device as recited in claim 7, comprising two side apertures sharing a common delivery lumen.

9. The interventional medical device as recited in claim 7, comprising a second side aperture and associated imaging lumen proximate said side delivery aperture and lumen.

10. The interventional medical device as recited in claim 1, further comprising at least one side aperture of the elongate body corresponding to an imaging lumen configured to image a human body in the vicinity of said side aperture during use of the device.

11. The interventional medical device as recited in claim 10, comprising two side apertures sharing a common imaging lumen.

12. The interventional medical device of claim 1 configured for intracardiac treatment via pericardial access without entry of the device through a blood vessel during use of the device.

13. An interventional medical device for pericardial access configured to perform minimally invasive surgical procedures comprising at least one ultrasound transducer, the device comprising
    an elongate body having no exterior delivery catheter or sheath configured to facilitate entry of a catheter through skin tissue of a human body, the elongate body configured to be introduced directly through a chest of the human body to the pericardium after a small stab incision on the skin during use of the device, the elongate body having proximal and distal ends and being tapered at the distal end to a distal tip having an end aperture, the distal tip of the elongate body having an outer diameter of a minimum of approximately 1 F, the tapered tip of the elongate body configured to form a conduit for the elongate body from a skin surface of the chest to a target site proximate the pericardium during use of the device;

an insertable needle configured to puncture a pericardial lining of the pericardium during use of the device;

a plurality of lumen extending through the elongate body, the plurality of lumen including one lumen for needle insertion and an imaging lumen, said one lumen for needle insertion extending through the elongate body to the end aperture at the distal tip of the elongate body;

said at least one ultrasound transducer being located at an outer periphery of the tapered tip of the elongate body near the distal end configured to provide images for guidance of movement of the elongate body from the chest to the target site proximate the pericardium of the human body and images of said puncture of the pericardial lining by said needle inserted in said one lumen for needle insertion as said insertable needle extends from said end aperture at said distal tip of the tapered tip of the elongate body during use of the device; and a luer lock near the proximal end of the elongate body for permitting a coupling of said one lumen for needle insertion to a syringe during use of the device.

14. The interventional medical device as recited in claim 13, the syringe for one of fluid removal and fluid delivery.

15. The interventional medical device as recited in claim 14, wherein the fluid comprises saline solution.

16. The interventional medical device as recited in claim 13 comprising first and second imaging lumen, a first imaging lumen for ultrasonic imaging and a second imaging lumen for fiber optic imaging.

17. The interventional medical device as recited in claim 13 further comprising at least one side aperture of the elongate body corresponding to a lumen configured for delivery to a human body in the vicinity of said side aperture during use of the device.

18. The interventional medical device as recited in claim 17 comprising two side apertures sharing a common lumen.

19. The interventional medical device as recited in claim 17 further comprising at least one side aperture of the elongate body corresponding to an imaging lumen configured to image a human body in the vicinity of said delivery side aperture.

20. An interventional medical device for pericardial access configured to perform minimally invasive surgical procedures comprising at least one ultrasound transducer, the device being a catheter configured for pericardial access during use of the device, the catheter comprising an elongate body having no exterior delivery catheter or sheath configured to facilitate entry of a catheter through skin tissue of a human body, the elongate body configured to be introduced directly through a chest of the human body to the pericardium after a small stab incision on the skin during use of the device, the elongate body having proximal and distal ends, the distal end of the catheter being tapered to form a distal tip of the distal end, the distal tip having an end aperture and having a minimal outer diameter of 1 F, the elongate body configured to be a conduit from a skin surface to a target site proximate the pericardium during use of the device;

an insertable needle configured to puncture a pericardial lining of the pericardium during use of the device;

a plurality of lumen extending through the elongate body, the plurality of lumen including one lumen for needle insertion, said one lumen for needle insertion having the end aperture at the distal tip of the elongate body for needle extension from the end aperture during use of the device, and a lumen for imaging during use of the device;

a plurality of apertures at the distal end corresponding to the plurality of lumen extending through the elongate body, the plurality of apertures comprising an aperture for imaging and the end aperture at the distal tip for needle extension from the end aperture configured to puncture the pericardial lining during use of the device, and said at least one ultrasound transducer being located at an outer periphery of the tapered tip of the elongate body near the distal end coupled to said imaging lumen and corresponding aperture, the at least one ultrasound transducer configured for providing images for guidance of movement of the elongate body from the chest to the target site proximate the pericardium of the human body and for providing images of said insertable needle extending from said end aperture, said insertable needle configured to puncture said pericardial lining during use of the device, the catheter configured for advancement to the pericardial lining and the insertable needle configured to be removed after said pericardial lining puncture during use of the device.

21. The interventional medical device as recited in claim 20, comprising first and second imaging lumen, a first imaging lumen for ultrasonic imaging and a second imaging lumen for fiber optic imaging.

22. The interventional medical device as recited in claim 20, further comprising at least one side aperture of the elongate body corresponding to a lumen configured for delivery to a human body in the vicinity of said side aperture during use of the device.

23. The interventional medical device as recited in claim 22, comprising two side apertures sharing a common lumen.

24. The interventional medical device as recited in claim 22, further comprising at least one side aperture of the elongate body corresponding to an imaging lumen configured for imaging a human body in the vicinity of said side delivery aperture during use of the device.

25. The interventional medical device of claim 20, wherein the elongate body is fabricated of a material selected from silicone, TEFLON, polyurethane, PVC, and elastomeric hydrogel.

26. The interventional medical device of claim 20, wherein the elongate body is substantially cylindrical in shape and has a maximum outer diameter of approximately 15 F.

27. The interventional medical device of claim 20, configured for performance of one of an epicardial mapping, lead placement and an intracardiac intervention via the catheter during use of the device.

28. The interventional medical device of claim 20, the tapered distal end configured for accessing the heart through the chest through the pericardium during use of the device.

* * * * *